US009730431B2

(12) United States Patent
French

(10) Patent No.: US 9,730,431 B2
(45) Date of Patent: Aug. 15, 2017

(54) AQUATIC ANIMAL PASSAGE WITH COUNTER

(71) Applicant: French Development Enterprises, LLC, N. Billerica, MA (US)

(72) Inventor: William L. French, Lexington, MA (US)

(73) Assignee: FRENCH DEVELOPMENT ENTERPRISES, LLC, N. Billerica, MA (US)

( * ) Notice: Subject to any disclaimer, the term of this patent is extended or adjusted under 35 U.S.C. 154(b) by 0 days.

(21) Appl. No.: 15/181,122

(22) Filed: Jun. 13, 2016

(65) Prior Publication Data
US 2016/0286766 A1    Oct. 6, 2016

Related U.S. Application Data

(63) Continuation of application No. 14/796,873, filed on Jul. 10, 2015, now abandoned, which is a
(Continued)

(51) Int. Cl.
*E02B 8/08* (2006.01)
*A01K 61/00* (2017.01)
(Continued)

(52) U.S. Cl.
CPC ............ *A01K 61/001* (2013.01); *A01K 61/90* (2017.01); *A01M 31/002* (2013.01); *E02B 8/08* (2013.01);
(Continued)

(58) Field of Classification Search
CPC . E02B 8/08; E02B 8/085; E02B 1/006; A01K 61/90; A01K 61/95
(Continued)

(56) References Cited

U.S. PATENT DOCUMENTS 853,146 A     5/1907   Von Gerstenbergk-Zech
1,594,578 A   8/1926   Thurlow
(Continued)

FOREIGN PATENT DOCUMENTS

EP    399870 A1    11/1990
JP    2005-090208   4/2005
(Continued)

OTHER PUBLICATIONS

International Search Report and Written Opinion for Int'l Application No. PCT/US2011/033643 entitled: Renewable Energy Systems, Date of Mailing: Oct. 27, 2011.
(Continued)

*Primary Examiner* — Frederick L Lagman
(74) *Attorney, Agent, or Firm* — Hamilton, Brook, Smith & Reynolds, P.C.

(57) ABSTRACT

A device for counting animal traffic in an aquatic animal passage system includes chutes positioned across the aquatic animal passage system and a sensor positioned to sense an animal moving through or in the aquatic animal passage system. The chutes and the aquatic animal passage system are formed with precast concrete segments and may include a protective liner or coating coupled to their outer surface to protect animals from contacting the outer surface of the precast concrete segments. The sensors may be integrated with the precast concrete segments forming the chutes. Smart concrete segments may be employed as transducers to create an electric field in the chutes, with impedance sensors coupled to the transducers being responsive to changes to the electric field in the chutes caused by passing animals.

10 Claims, 18 Drawing Sheets

Related U.S. Application Data continuation-in-part of application No. 13/827,020, filed on Mar. 14, 2013, now Pat. No. 9,103,084, which is a continuation-in-part of application No. 13/225,990, filed on Sep. 6, 2011, now Pat. No. 8,414,223, which is a continuation-in-part of application No. 13/092,855, filed on Apr. 22, 2011, now abandoned.

(60) Provisional application No. 61/477,360, filed on Apr. 20, 2011, provisional application No. 61/327,500, filed on Apr. 23, 2010.

(51) Int. Cl.
    *G01N 27/02*      (2006.01)
    *A01M 31/00*      (2006.01)
    *A01K 61/90*      (2017.01)

(52) U.S. Cl.
    CPC ............ *E02B 8/085* (2013.01); *G01N 27/02* (2013.01); *G01N 27/028* (2013.01)

(58) Field of Classification Search
    USPC .......................................................... 405/81
    See application file for complete search history.

(56) References Cited

U.S. PATENT DOCUMENTS

| | | |
|---|---|---|
| 1,628,933 A | 5/1927 | Troiel |
| 1,898,095 A | 2/1933 | Noetzli |
| 2,138,070 A | 11/1938 | Parkinson et al. |
| 2,138,071 A | 11/1938 | Parkinson et al. |
| 2,515,059 A | 7/1950 | Rowbotham |
| 2,566,748 A | 9/1951 | Hall |
| 2,961,731 A | 11/1960 | Buzzell et al. |
| 3,342,033 A | 9/1967 | Crouch et al. |
| 4,031,676 A | 6/1977 | Dally |
| 4,260,286 A | 4/1981 | Buchanan |
| 4,468,153 A | 8/1984 | Gutierrez Atencio |
| 4,493,587 A | 1/1985 | Ferrari |
| 4,740,105 A | 4/1988 | Wollander |
| 4,998,846 A | 3/1991 | Evstratov et al. |
| 5,161,913 A | 11/1992 | Boylan |
| 5,439,316 A | 8/1995 | Richardson |
| 5,817,944 A | 10/1998 | Chung |
| 6,012,872 A | 1/2000 | Perry et al. |
| 6,042,301 A | 3/2000 | Sovran |
| 6,155,746 A | 12/2000 | Peters |
| 6,273,639 B1* | 8/2001 | Eikrem ................... E02B 8/085 119/203 |
| 6,281,597 B1 | 8/2001 | Obermeyer et al. |
| 6,942,423 B2 | 9/2005 | Davis |
| 7,708,495 B1 | 5/2010 | Antee |
| 8,414,223 B2 | 4/2013 | French |
| 9,103,084 B2 | 8/2015 | French, Sr. |
| 2002/0018696 A1 | 2/2002 | Robinson |
| 2002/0031401 A1 | 3/2002 | Yang |
| 2004/0009040 A1 | 1/2004 | Boylan |
| 2004/0234218 A1 | 11/2004 | Tac |
| 2004/0265060 A1 | 12/2004 | Lee et al. |
| 2005/0074289 A1 | 4/2005 | Tucker |
| 2006/0078388 A1 | 4/2006 | Obermeyer |
| 2007/0116522 A1 | 5/2007 | Boudreaux, Jr. |
| 2007/0154265 A1 | 7/2007 | Stauffacher et al. |
| 2008/0075535 A1 | 3/2008 | Han |
| 2008/0089743 A1 | 4/2008 | Han |
| 2008/0240861 A1 | 10/2008 | Phillips |
| 2009/0041543 A1 | 2/2009 | Kroger |
| 2010/0045311 A1 | 2/2010 | Chung |
| 2010/0270811 A1 | 10/2010 | Angulo Valpreda et al. |
| 2011/0146802 A1 | 6/2011 | Feher |
| 2012/0009018 A1 | 1/2012 | Marquis |
| 2012/0087733 A1 | 4/2012 | French, Sr. |
| 2013/0236249 A1 | 9/2013 | Greif |
| 2014/0356070 A1 | 12/2014 | Stromotich |
| 2015/0247300 A1* | 9/2015 | Seo ........................... E02B 7/18 405/83 |

FOREIGN PATENT DOCUMENTS

| | | |
|---|---|---|
| KR | 10-2006-0025314 | 3/2006 |
| KR | 10-2008-0077937 | 8/2008 |
| KR | 10-2009-0047190 | 5/2009 |

OTHER PUBLICATIONS

International Preliminary Report on Patentability for Int'l Application No. PCT/US2011/033643 entitled: Renewable Energy Systems, Date of Mailing: Nov. 1, 2012.

International Search Report and Written Opinion for Int'l Application No. PCT/US2014/020640, entitled: Intelligent Hydroelectric Dam With Power Storage, Date of Mailing: May 30, 2014.

Notification Concerning Transmittal of International Preliminary Report on Patentability. Date of Mailing: Sep. 24, 2015 (PCT/US2014/020640).

Office Action for U.S. Appl. No. 14/796,873, Mailed on Jan. 15, 2016.

\* cited by examiner

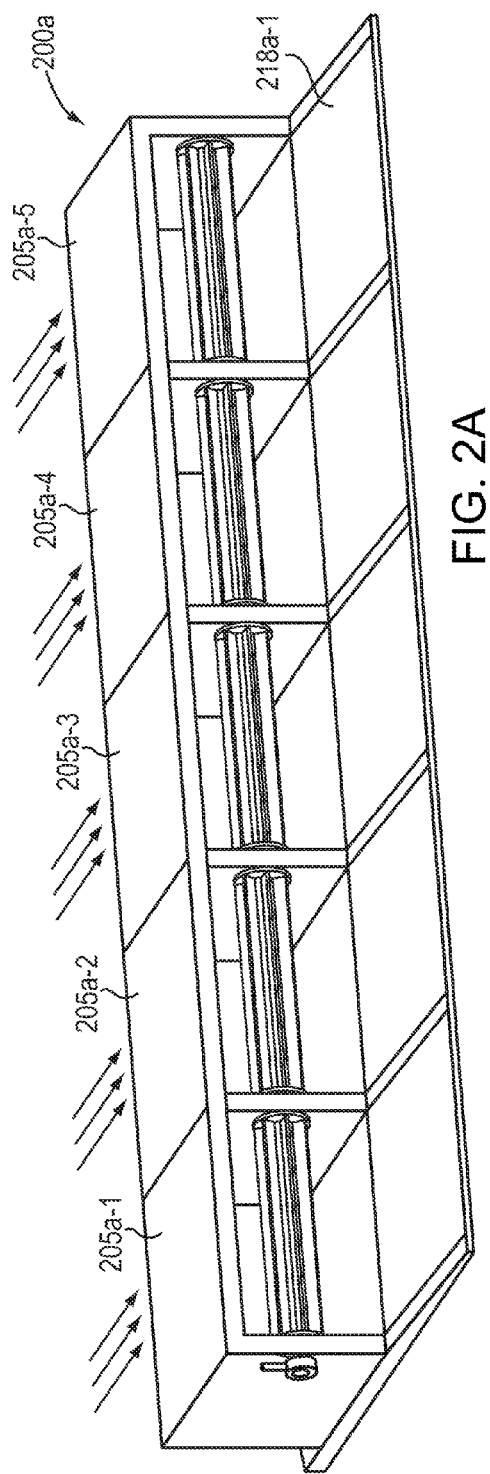
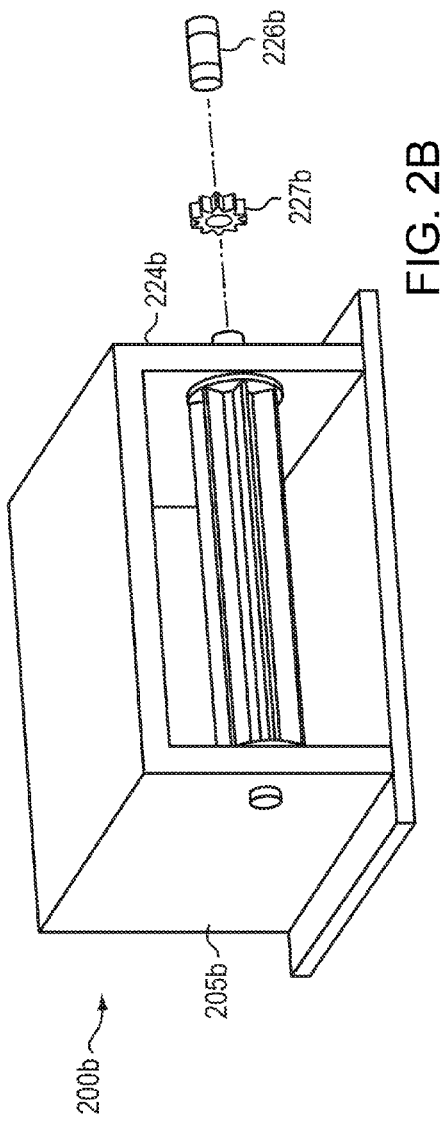
FIG. 2A
FIG. 2B

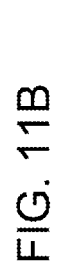
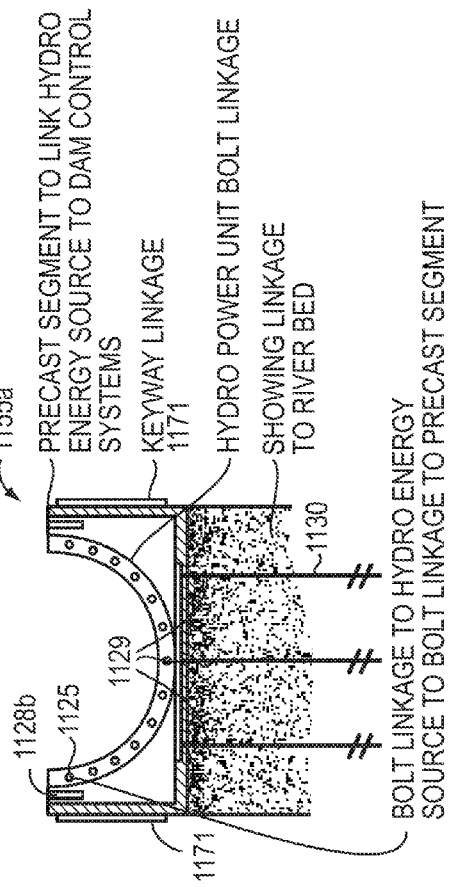
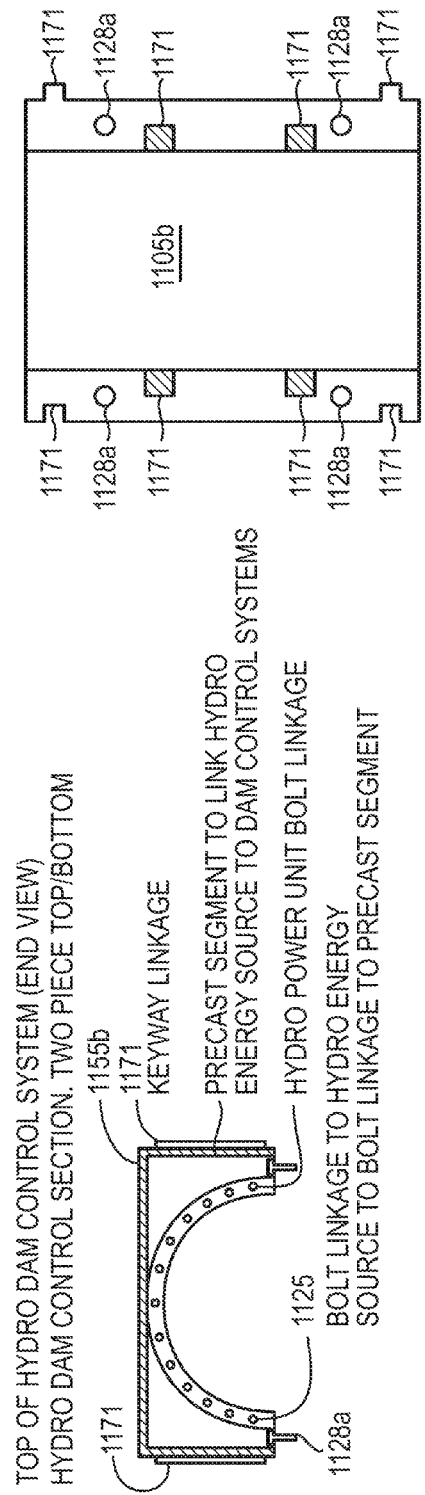
FIG. 11A
FIG. 11B
FIG. 11C

SIDE VIEW

TOP VIEW

AQUATIC ANIMAL PASSAGE WITH COUNTER

RELATED APPLICATIONS

This application is a Continuation of application Ser. No. 14/796,873 filed Jul. 10, 2015, now abandoned, which is a Continuation-in-Part of U.S. application Ser. No. 13/827,020, filed on Mar. 14, 2013, now U.S. Pat. No. 9,103,084, which is a Continuation-in-Part of U.S. application Ser. No. 13/225,990, filed on Sep. 6, 2011, now U.S. Pat. No. 8,414,223, which is a Continuation of application Ser. No. 13/092,855, filed on Apr. 22, 2011, now abandoned, which claims the benefit of U.S. Provisional Application No. 61/477,360, filed on Apr. 20, 2011, and which claims the benefit of U.S. Provisional Application No. 61/327,500, filed on Apr. 23, 2010, each entitled "Intelligent Hydroelectric Dam with Power Storage" by William L. French, Sr. The entire teachings of the above applications are incorporated herein by reference.

BACKGROUND OF THE INVENTION

Hydroelectric dams provide electrical power through use of converting kinetic energy provided by running water into electrical power through use of rotation-to-electric converters, as well known in the art. An example of such a dam is the Hoover Dam that provides great amounts of electrical power for providing electricity to a grid that is configured to distribute electrical energy to a local area. As well understood in the art, to install a dam requires discontinuity of the flow of water over the portion of land at which the dam is to be placed such that pouring of concrete and curing of the concrete may be done, with installation of power generation components to be completed prior to redirecting the water flow back to the dam.

SUMMARY OF THE INVENTION

An example embodiment of the present invention includes precast segments configured to be interconnected to other precast segments to compose a dam, and may also include a main energy generation component, which may be operably interconnected to the interconnected precast segments. The main energy generation component is configured to be coupled to an energy transfer bus. At least one interlocking element is configured to interconnect the precast segments.

Another example embodiment of the present invention includes a method for interconnecting precast segments, where the precast segments may be operably interconnected to an energy generation component, which is coupled to an energy transfer bus, and interconnected to each other via at least one interlocking element.

A further example embodiment of a dam, and corresponding method of assembly, includes an existing dam structure, at least two precast segments of the dam configured to be interconnected, and at least one interlocking element or structure configured to join the at least two precast segments to encase the existing dam structure and form the dam at a dam location.

A still further example embodiment of a dam, and corresponding method of assembly, includes at least two precast segments of the dam configured to be interconnected, and at least one interlocking element or structure configured to join the at least two precast segments to encase a main energy generation component and form the dam at a dam location.

An example embodiment of the present invention includes a device for counting animal traffic in an aquatic animal passage system, the device comprises one or more chutes positioned across the aquatic animal passage system, the one or more chutes and the aquatic animal passage system are formed with precast concrete segments, and the one or more sensors are positioned to sense an animal in the aquatic animal passage system, with the one or more sensors being responsive to animals moving through the one or more chutes and sensing at least one of: a number of animals and a volume of animals traveling through the aquatic animal passage system.

BRIEF DESCRIPTION OF THE DRAWINGS

The foregoing will be apparent from the following more particular description of example embodiments of the invention and as illustrated in the accompanying figures. The drawings are not necessarily to scale, emphasis instead being placed upon illustrating example embodiments of the present invention.

The accompanying figures, where like reference numerals refer to identical or functionally similar elements throughout the separate views and which together with the detailed description below are incorporated in and form part of the Specification, serve to illustrate various embodiments further and to explain various principles and advantages all in accordance with the example embodiments of the present invention. The teachings of all patents, published applications and references cited herein are incorporated by reference in their entireties.

FIG. 2A is a mechanical diagram of multiple segmental precast dam components arranged together to form a composite dam.

FIG. 2B is a view of a single precast dam having a hydroelectric energy generation system and a gearing system to change a rate of rotation of the electrical generator for a given rate of waterflow.

FIGS. 11A-11C illustrate various views of precast segments according to an embodiment of the present invention.

FIG. 14A-2 is an illustration of an aquatic animal passage system including precast cement base sections in an offset configuration.

DETAILED DESCRIPTION OF THE INVENTION

Figure 1A:
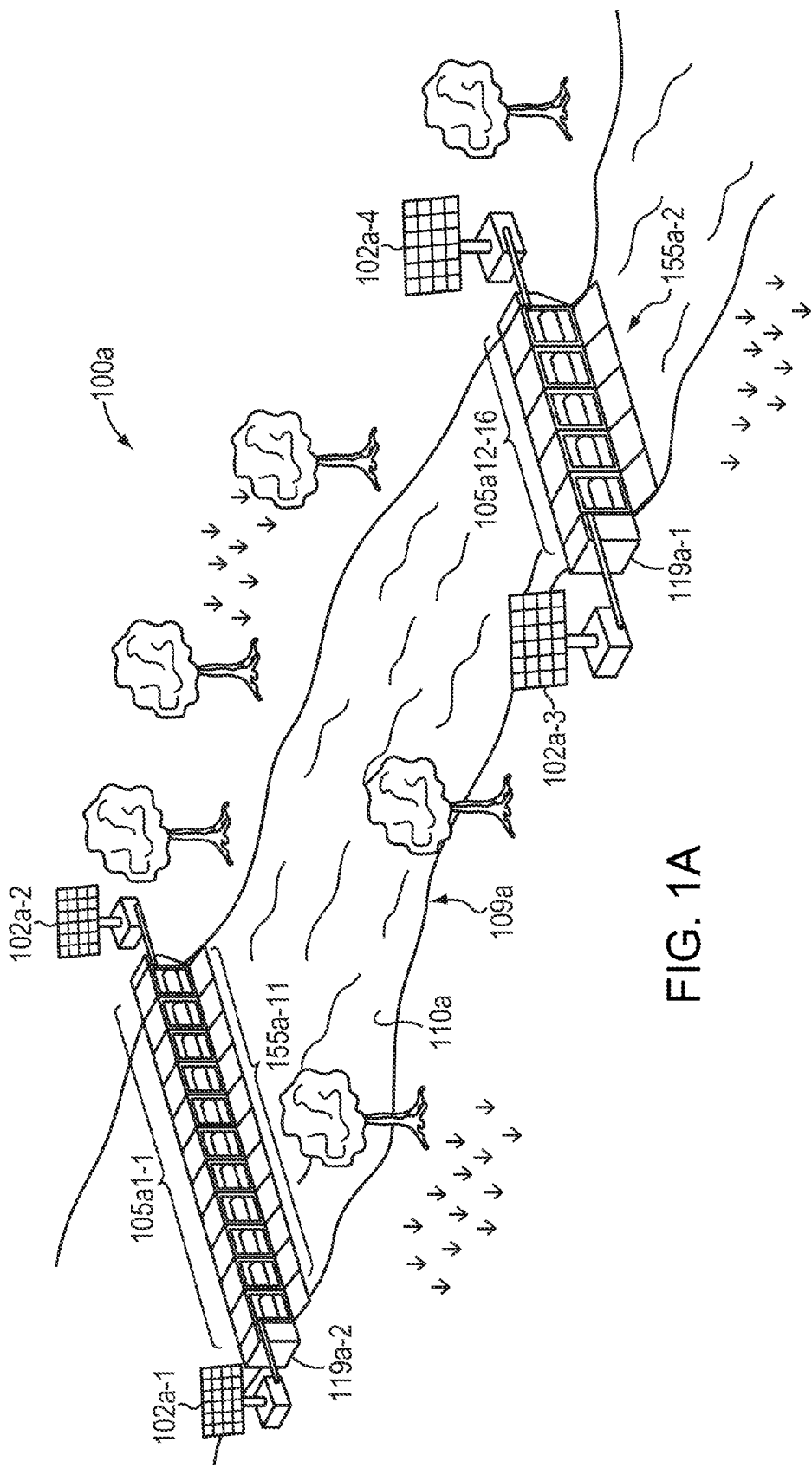
FIG. 1A is a high level view of a river in which multiple dams according to embodiments of the present invention may be employed, optionally including auxiliary power systems, such as solar panel auxiliary power systems.

A description of example embodiments of the invention follows.

An embodiment of the present invention includes precast dam components that may be installed at a dam location, either with water flow diverted or while water flow continues, depending on the strength of the water flow.

An embodiment of the invention may include an underpinning system that has elements of concrete or other materials formed in the shape of large pins that are positioned vertically into the ground at which the dam is to be located and having a diameter configured to match a diameter of a hole defined by a lower surface of the dam component, such as a precast dam component, to be installed at the location of the underpinning elements.

A spillway extender may be provided to prevent downstream erosion, where the spillway extender is configured to be integrally coupled to the precast dam components such that waterflow immediately downstream of the precast dam components do not cause the surface of riverbed to erode away, which may result in an instability of the dam components.

An adjustable pressure gate may be included or integrated into precast dam components such that water flow rate and pressure may be raised or lowered in any manner desired, such as to maintain a constant pressure across a turbine in the precast dam components during periods having a lower or expectedly lower rainfall or other precipitation such that the river or reservoir has a lower water height than usual. The gate may be mechanically, manually, or electrically adjustable.

The dam may further include an intelligent gear shifting apparatus that is used to change gears of the turbine or other rotational components such that the rotational forces may be increased or decreased in a manner most effective to translating the rate of waterflow across the rotational element to produce higher or lower conversion of rotation to electricity. A control system having intelligence may be employed to shift the gears in an adaptive manner.

In addition to the main energy generation turbines or other rotational elements used to generate energy, auxiliary energy generation sources may be employed to provide energy for electrical components at the dam, where such auxiliary energy generation systems may include upstream or downstream mini-turbines or even solar panels configured at either side of a river at the dam.

In the case of precast dam components, the precast dam components may be configured as square or rectangular or other geometrical shaped structures that have interlocking features to enable multiple precast dam components to be interlocked together to form a unified dam. The interlocking features may include, for example, any male/female features known in the art, such that construction of the dam of the multiple components may be done quickly and efficiently at the site. Dividers upstream or downstream of the interlocking dam features and, in one embodiment, above spillway extenders associated with the dam or segmental components, may be provided to form multiple segmental spillways, which may add to longevity of the dam. Keyways may be employed to provide an interlocking feature for a male feature of the dividers such that good alignment with vertical walls of the segmental dam components may be provided and maintained. The dividers having an angle opening in a downstream direction may also or alternatively be provided on the upstream side of the dam to prevent debris or other objects from damaging or dislodging any of the segments of the dam or energy generation components therein.

FIG. 1A is a high level diagram 100*a* of a river 110*a* in which multiple dams according to embodiments of the present invention may be employed, optionally including auxiliary power systems, such as solar panels 102*a*-1 ... 4 auxiliary power systems. Alternative example embodiments may include additional or different auxiliary power systems, such as wind turbines or mechanically powered systems. FIG. 1A further illustrates a river at which two dams 155*a*-1,2 with power generation devices, such as turbines or water wheels (not shown), may be employed. In the diagram 100*a*, the dams 155*a*-1,2 have associated therewith other power generators, referred to herein as auxiliary generators, which may be in the form of solar panels 102*a*-1 ... 4 or auxiliary water wheels (not shown).

During assembly of the dams, the precast segments 105*a*-1 ... 16 may be deployed while the river 110*a*, or other body of water, is flowing or while the river is diverted in some other path, depending upon the flow rate of the river, as should be understood in the art. The river bed 109*a* may be fitted with an underpinning system (not shown), such as vertically arranged cement rods or metallic rods that extend a certain depth into the riverbed, such as 6 feet or 20 feet, depending on the expected strength of the river, such that they may support the precast dam structure(s) to maintain the dams' segmental and collective positions in the riverbed. The precast structures 105*a*-1 ... 11 and 105*a*-12-16 may individually (i.e., 105*a*-1, -2, ... , -16) define interlocking male or female components (not shown) such that they may be integrally configured with the underpinning elements (not shown).

The dams 155*a*-1,2 themselves may have single or multiple energy storage elements 119*a*-1,2, such as batteries, that may accept electrical power or energy generated by the power generating elements associated with the dams 155*a*-1,2, from which energy may later be drawn for use in various applications, such as those involved with generating power at the dam or used to provide electricity for residences (not shown), municipals, or power grids. Inverters (not shown) may be employed to convert DC power of the energy storage elements 119a-1,2 to AC power, or AC power may be provided directly by the turbines of the dams.

Because a dam may be formed of multiple precast dam components, construction and assembly of the dams is significantly reduced such that multiple dams along a river, optionally in very close proximity, may be provided at significantly lower cost than were a single, large, dam structure and associated power generation and storage equipment constructed on the same waterway. Such reduction in costs may lend itself to a distributed energy power generation/storage/delivery system that may be more convenient, economical, and otherwise useful to a local or widespread region.

Figure 1B:
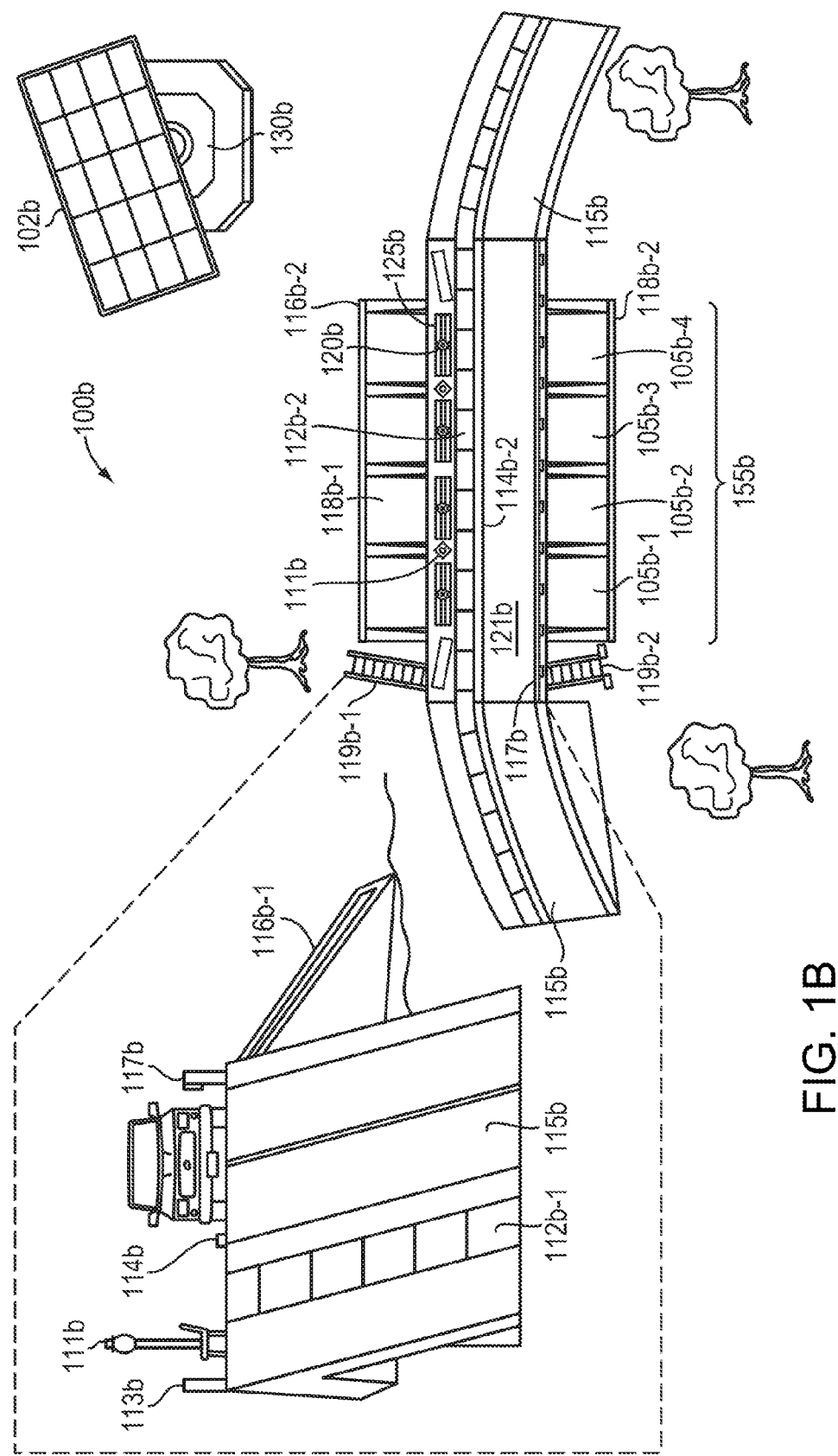
FIG. 1B is a high level view of a dam according to an example embodiment of the present invention optionally including segmented ballast base support structures.

FIG. 1B is a high level diagram 100b of an example embodiment of the present invention that illustrates an upstream water control system interconnected to a precast segmented access path for traversing and interacting with the dam system. The diagram 100b illustrates an assembled dam 155b of an embodiment of the present invention including interconnected precast dam structures 105b-1 . . . 4. The precast structures 105b-1 . . . 4 may further include buttress walls 116b-1-2, which may be configured to include suction capabilities and may be connected to or located near spillways 118b-1,2. The spillways 118b-1,2 may be segmental precast constructs, which may be assembled during or after the assembly of the dam or dam segments. The dam 155b may further include or be interconnected with precast sections of additional segmental structures, such as walkways or roadways, which may be linked using a bolt linkage system, keyway method, or other known interlocking method.

The dam 155b may further include an energy source, such as solar panel 102b, which may include a land or ground mounted dual axis solar tracking system. Details of a dual axis solar tracker are described further in Applicant's pending U.S. Patent Application (Serial Number not yet assigned) being filed concurrently herewith, entitled "Dual Tower Solar Tracker System" by William L. French, Sr., which claims priority to U.S. Provisional Application No. 61/477,354 filed on Apr. 20, 2011, and is related to and incorporated by reference U.S. Provisional Application No. 61/327,500 filed on Apr. 23, 2010 entitled "Dual Tower Solar Tracker System" by William L. French, Sr.; the entire teachings of the above applications being incorporated herein by reference in their entireties. Continuing to refer to the example embodiment of FIG. 1B, the dam 155b may further include or be interconnected with a water gate control unit 120b and/or an adjustable water gate 125b, which may be operated individually or simultaneously.

The example embodiment of the dam 155b of FIG. 1B may include a segmented ballast base support system that may be configured on, around, or over unstable ground in a manner providing for a precast access ramp 115b that may be implemented to connect opposite embankments of the waterway through which the dam is located. The segmented precast support system may further allow for a fish ladder (or fishway) 119b to pass through or down the structure surrounding the dam system so as to enable fish to pass around the barrier to the waters on the other side of the dam. The precast access ramps may interconnect an access road 121b that may be constructed on location using precast segmental system. Details of the segmented ballast base support structure are described further in pending U.S. patent application Ser. No. 12/658,608 filed on Feb. 9, 2010, entitled "Segmented Ballast Base Support Structure and Rail and Trolley Structures for Unstable Ground" by William L. French, Sr. The entire teachings of which are incorporated herein by reference.

The precast segmented support structure system and method may be used to incorporate a precast guard rail 117b, precast spillway with buttress wall 116b, precast curb 114b, splash wall 113b, or public or private walkway 112b, and any or all of which may be surrounded by or laid on top of an uneven or unstable ground structure, such as grass, mud, slanted ground, etc.

FIG. 2A is a mechanical diagram 200a of multiple segmental precast dam components arranged together to form a composite of the segmental dam 205a-1 . . . 4. FIG. 2A illustrates the waterflow 208a to a dam formed of the precast segments 205a-1 . . . 4. The precast segments 205a-1 . . . 4 may be interlocked in any way understood in the art, such as through composite component structures precast into the cement, affixed into the precast cement, or otherwise understood in the art, including elements coupled to the precast structures after the precast structures have been formed. A mechanical knob, leaver, or other device (not shown) may be provided with the collective or component structure(s) to raise and lower turbines or other rotational elements in the dam to accommodate the height of water flowing therethrough. Further, mechanical elements may be provided to raise and lower gates associated with the collective dam or components thereof such that the height of water flowing into or out of the dam may be controlled mechanically. It should be understood that automated electrical raising and lowering of the rotational elements or gates may also be employed, where sensors and activation elements, such as linear or rotational motors and motion support assemblies, may also be employed. It should be understood that any electronics or mechanical elements may be sufficiently protected against the elements, particularly in the environment of water and water-related elements.

FIG. 2B is a diagram 200b of a single precast dam (e.g., dam component) 205b having a hydroelectric energy generation system and a gearing system 227b to change a rate of rotation of the electrical generator for a given rate of waterflow. The mechanical diagram 200b is a single segment for hydroelectric energy generation system that may be used in a multiple segmental group to define a dam on a waterway of arbitrary width. The diagram of FIG. 2B further includes an indicator of a gear system 227b that may be used to change the rate of rotation of any rotational elements used in the power generation portion of the dam. The diagram also includes an indication of a shaft or shaft system 226b to transfer mechanical energy to electrical energy (transformer not shown) such that electrical energy is produced and transferred via electrical cables (not shown) or other conductive components to a battery storage or otherwise to a power distribution system to reach an end user.

Figure 2C:
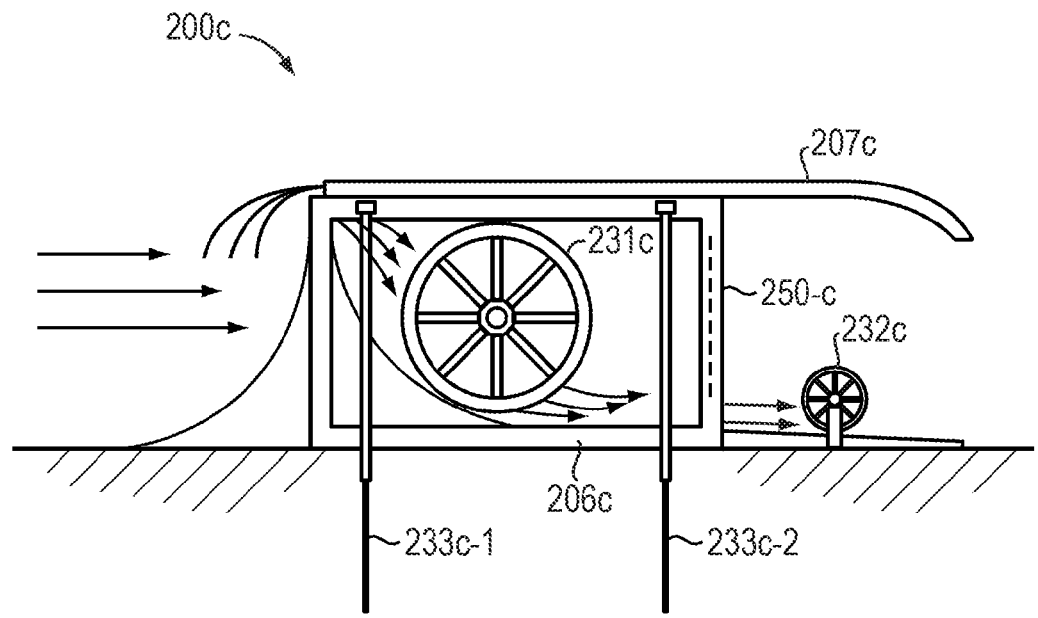
FIG. 2C is a side view of a dam according to an embodiment of the present invention in which a rotary wheel used for converting waterflow to electrical energy is employed, where the waterflow travels beneath the wheel to cause a rotation and optionally causes an auxiliary wheel to rotate to generate auxiliary power.

FIG. 2C is a side view 200c of a dam according to an embodiment of the present invention in which a rotary wheel (e.g., a turbine) 231c used for converting waterflow to electrical energy is employed, where the waterflow travels beneath the wheel 231c to cause a rotation, and, optionally, causes auxiliary wheels, such as auxiliary wheel 232c, to rotate to generate auxiliary power. The example embodiment of FIG. 2C further illustrates water flowing from left to right over a vertical component of an upstream side of the segmental dam and beneath (or over) a water wheel or turbine or other rotational element in a manner causing rotation of the rotational element, which, in turn, causes a movement of an electromagnetic component with respect to another electromagnetic component in a manner known to generate electricity. The example embodiment of FIG. 2C further illustrates an auxiliary wheel 232c to generate electricity for use in providing power for electrical components used at the dam, itself. FIG. 2C further includes vertical elements 233c-1,2 that extend from beneath the riverbed through a floor 206c of a dam component to a ceiling 207c of a dam component such that the vertical elements 233c-1,2 provide structural stability and reinforcement against the dam's moving along the riverbed while water is at a high rate of flow.

Example embodiments of the vertical elements 233c-1,2 may further provide structural stability from ground movement, water pressure, wind flow, and other external or internal factors that can affect the structural integrity or stability of the dam components. The vertical elements, for example, pins, may be any diameter, length or shape, configured to be interconnected with the precast dam component 205c. Further, as shown, the precast dam component 205c may include other precast dam elements that form upstream or downstream features associated with the dam components such that upstream or downstream erosion of the riverbed does not occur or is otherwise minimized. For example, a spillway extender, such as the spillway system 218a-1 illustrated in FIG. 2A, being downstream or upstream of the dam component may extend many feet, such as 10 feet or more, in certain river situations.

Figure 2D:
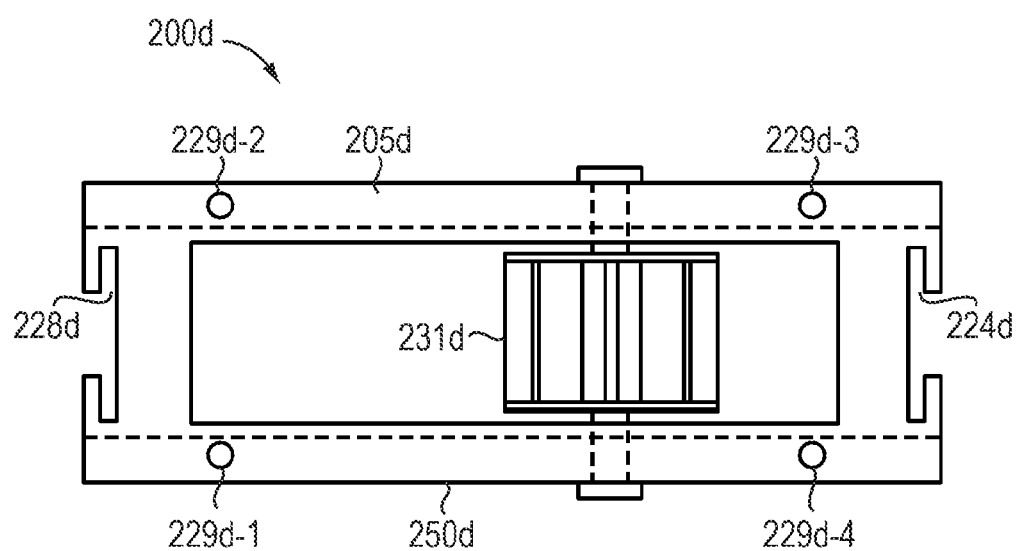
FIG. 2D is a top view of a single precast segment of a hydroelectric dam system that illustrates features fore and aft of the dam to interlock the precast segment with other precast segments or spillway extenders.

FIG. 2D is a diagram 200d of a top view of a single precast segment 205d of a hydroelectric dam system that illustrates features fore and aft of the dam to interlock the precast segment with other precast segments, spillway extenders, or other interlocking components. FIG. 2D further illustrates an example configuration of a water wheel or turbine 231d within the precast structure and illustrates other structural features of the precast structure. For example, the precast structure may define holes 229d-1 . . . 4 through which pins extending into the riverbed and up through the bottom (e.g., floor) and, optionally, the top (e.g., ceiling) of the precast structure may be provided. The holes 229d-1 . . . 4 may be oversized and filled-in with cement or other filler (not shown) such that ease of integration and deployment may be experienced at the site of installation. In alternative example embodiments, the holes 229d-1 . . . 4 may be integrated into the precast structure 205d or may be later installed or carved out as needed during onsite or offsite installation or interconnection. The fore and aft of the precast structure 205d may include slots 228d and 224d such that upstream and downstream components, such as spillway extenders (not shown), may be structurally or mechanically coupled to the precast segment 205d in a simple, convenient, and structurally sound manner. Although not illustrated, slots to interconnect the precast segment with other precast segments may be provided on the sides, top, or bottom of the precast structure, where the slots may run parallel to or perpendicular with the river flow.

Figure 3:
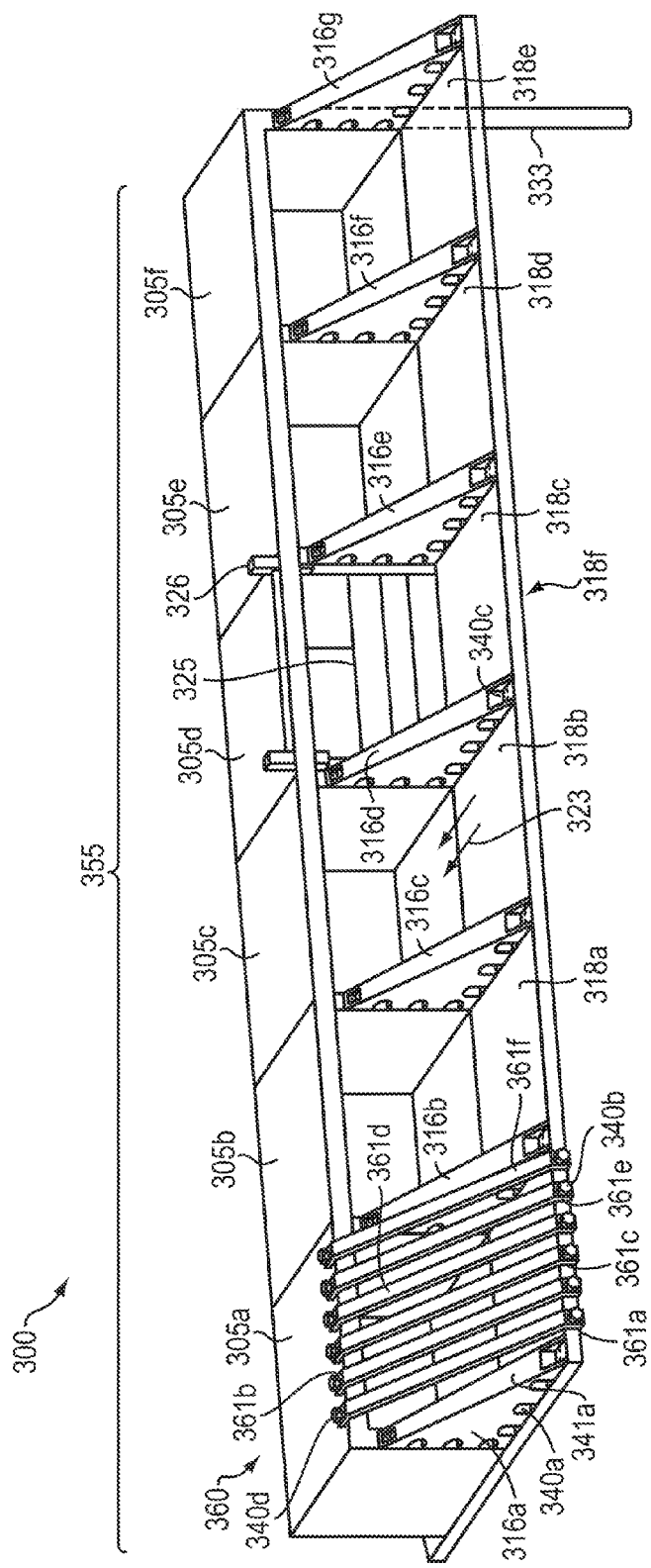
FIG. 3 is a mechanical diagram illustrating upstream and downstream spillway structures that may be precast and assembled along with the precast segmental dam structures.

The slots 228d and 224d and corresponding mating-shaped pintles (now shown) on other segments may be interchangeably referred to herein as "interlocking elements." Alternatively, separate mechanical elements (not shown) may be provided as interlocking elements, where the precast segments may have the same slots 228d and 224d and an interlocking element slide into neighboring slots simultaneously to form a solid mating of adjacent precast segments FIG. 3 is a mechanical diagram 300 illustrating upstream and downstream spillway structures that may be precast and assembled along with the precast segmental dam structures. The mechanical diagram 300 illustrates multiple precast segments 305a-f inter-connected with each other to form a dam 355 in the collective. The dam 355, as illustrated, includes no gaps between each of the precast segments 305a-f so as to force all water (not shown) through the water flow pathways, such as waterflow pathway 323 of the precast segment 305b, defined by each of the precast segments, thereby ensuring all water contributes to the rotation of the power generators (not shown) within each of the segments. It should be understood that the power generators may be positioned in the precast segmental structures in a manner using all or just a portion of the water flowing through the precast segments and that certain ones of the precast segments may, alternatively, not be equipped with power generating components.

Continuing to refer to FIG. 3, the example embodiment also shows tapering (or increasing, depending on one's perspective) dividers 361a-f between segments that are configured above the spillways 318a-e and aligned with vertical walls, such as the vertical buttress or brace walls 316a-g of the segmental dam components. The example embodiments of dividers 361a-f may be precast as part of a debris protection system 360 and installed as may be warranted via linkages, such as a bolt system 340a-d, for example, where the dividers may be galvanized H beam dividers. The dividers 361a-f are typically positioned on the upstream side of the dam such that any downstream-flowing debris or structures, such as boats or swimmers, ride up above the dam to prevent damage to the dam, segmented components of the dam, power generation devices therein, or other elements interconnected to the dam. Thus, flowing water that forces debris, such as large branches, will push the debris upward on top of or over the dam rather than into vertical buttresses of the dam or power generation devices in the dam. This makes for a longer life dam structure than were the dividers not provided.

Alternative example embodiments of the dividers 361a-f may provide for dividers consisting of a variety of materials, shapes, lengths, and other attributes as may be favorable based on the dam location. In alternative example embodiments of the present invention, the dividers may be separately installed into slots, pathways, or other such areas of the precast segments in such a manner as to include a malleable element, such as a spring or shock absorbing component, such that the dam or dam components receive less of an impact of flowing or moving debris, thereby allowing for a more structurally sound dam. It should be understood that the dividers may be placed in some or all of the precast segments at varying or similar configurations, angles, widths, etc.

Alternative example embodiments of example embodiment of FIG. 3 may include a shaft control system 326 to provide for the operation of a water gate 325 as a mechanism for allowing or prohibiting the free flow of a liquid (e.g., water) through the precast segments via the waterflow pathway (e.g., waterflow pathway 323) in a manner that enables controlled operation. The shaft control system 326 may be operated manually, automatically, or in any such manner preferable on a per-site or dam location basis.

Figure 4:
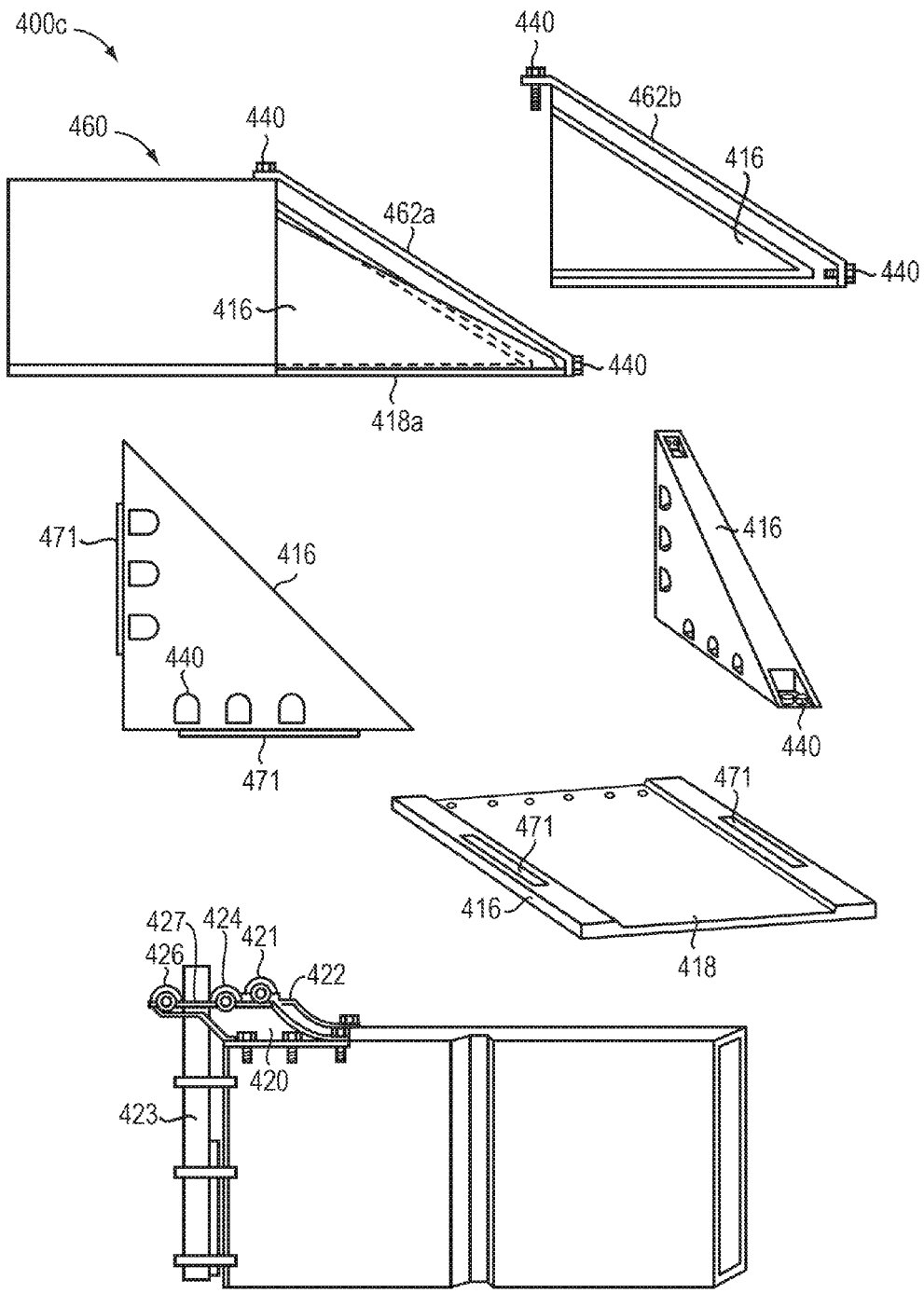
FIG. 4 is a group of mechanical diagrams illustrating spillway structural elements, including vertical and horizontal elements, which may include keyway lock and support structures.

FIG. 4 is a group of mechanical diagrams 400 of spillway structural elements, including vertical and horizontal elements, which include keyway lock and support structures. The mechanical diagrams 400 further illustrate embodiments of features in the spillways and vertical components of the segments of the dam to enable the dividers, such as dividers 361a-f of FIG. 3, to interlock with the dam in a manner maintaining as much integrity as possible and in a manner that allows for ease of assembly at the site of the dam. The dam may be configured and/or assembled to include a section including a debris shield system 460 that includes dividers, such as H beams, 462a-b. The components and/or elements of the dam may be interconnected using linkage bolts 440 and/or other linkage element(s) to form a linkage system. The linkage system may be configured to interlock multiple components using the same or different dimensions and positions of the interconnection systems.

Alternative example embodiments of the diagrams 400 may include additional locking mechanisms, such as the keyway lock and support system 471, for providing structural integrity and reinforcement to the sides, bottoms, and tops of the dam component elements. The keyway locking mechanisms may be interconnected via different methods; for example, the keyway locks may include a female and male component that may be interlocked. Additional elements may be employed to provide manual and/or automatic control for the dam employing control gates, gears, shafts, and other control devices currently known or hereinafter developed as applicable to a dam or dam component. Such elements are usually located on the upstream side of the dam; however, alternative embodiments of the present invention may have the dam components, elements, and precast structures arranged in various or adjustable configurations based on any number of external or internal factors, such as varying weather patterns at the dam location.

The example embodiment of FIG. 4 may include a unit 421 for lifting and lowering the control gears, which may be operably interconnected to a gear plate 427. The example embodiment of the controls may further include a shaft 424 employing interlocking techniques, such as using a keyway locking mechanism, optionally interconnected to guide roller 425 and/or a control gate support bracket 422 for enabling movement and control of the system. Alternative example embodiments may include features originally integrated into the precast structures or elements configured to be later applied or constructed to the precast structure(s).

Figure 5:
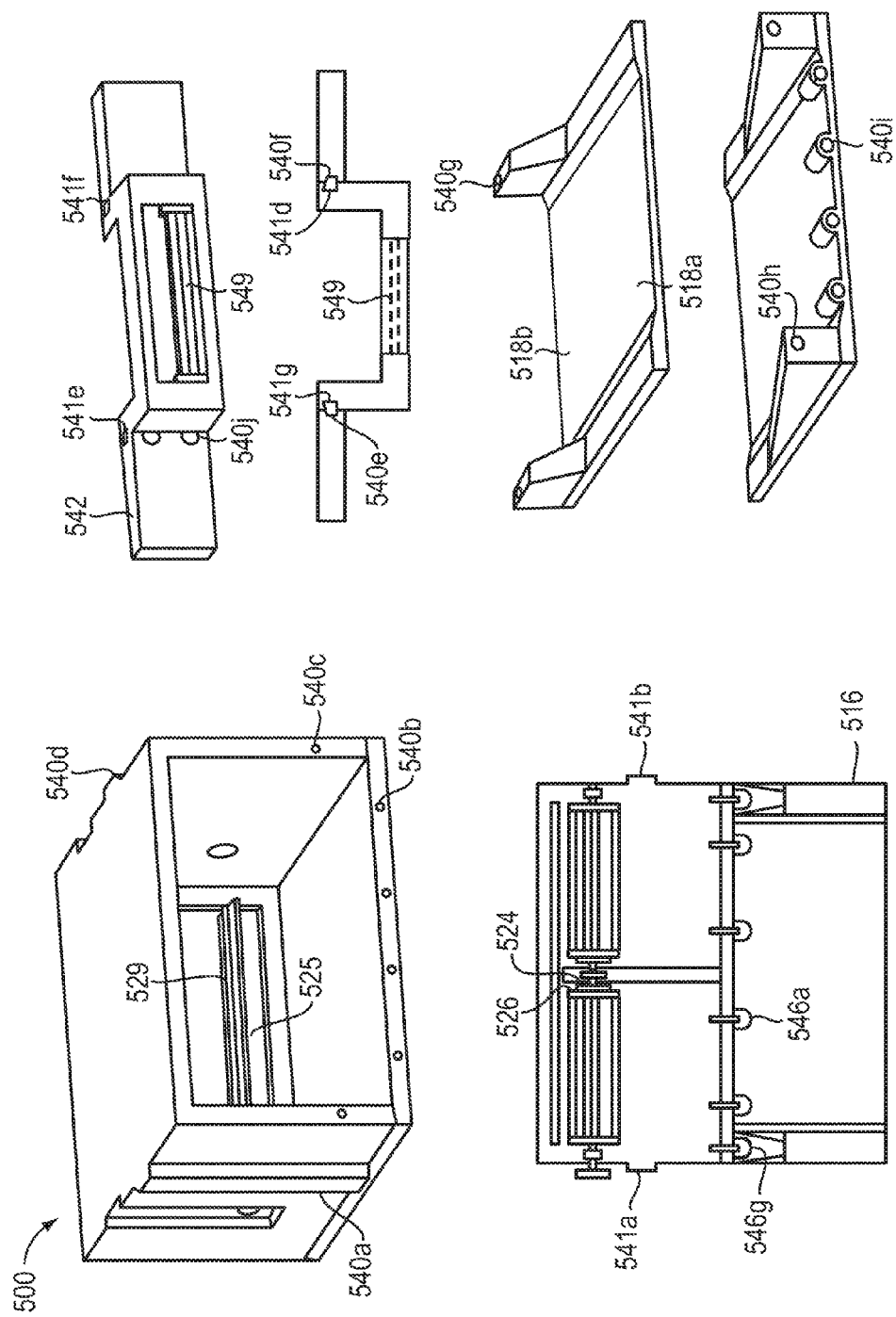
FIG. 5 is a group of mechanical diagrams illustrating alternative features and embodiments of the dam assembly according to embodiments of the present invention.

FIG. 5 is a group of mechanical diagrams 500 illustrating alternative features and embodiments of the dam assembly according to embodiments of the present invention. FIG. 5 includes multiple aspects of the precast segmental dam components, such as the turbine system, linkages between segments 540a-i, interconnecting features between segments 541a-g, adjustable wooden board gate system 549 or other material for water height or flow control, spillway 516 and spillway segments 518, linkage features between the spillway and segments 546, interconnecting linkages between cement or metal components of the segments and/or spillways, and example sizes of the precast structures. Further system components may include a water gate 529 to adjust water flow (for example, such as the water gate 529 being in an open position 525 thereby allowing water to flow through at different rates), and shaft and drive hole for interconnecting pinning elements on the top, sides, and bottom of the precast segments. It should be understood that the sizes of any of the dam components may vary such that they are suitable for the width, depth and flow rate of the waterway and provide ease of transportation, deployment, and interlocking assembly at the site of the dam.

Figure 6:
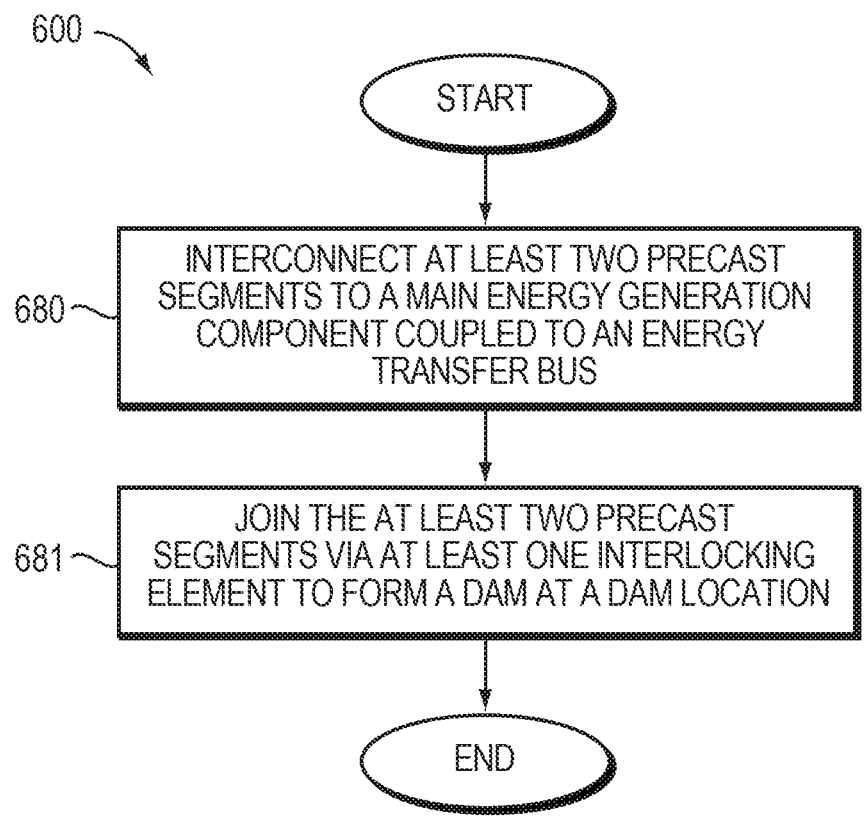
FIG. 6 is a flow diagram of an embodiment of the present invention that illustrates a method of dam assembly.

FIG. 6 is a flow chart 600 of an embodiment of the present invention that illustrates a method of dam assembly. The flow diagram 600 allows for a method of interconnecting at least two precast dam segments to a main energy generation component coupled to an energy transfer bus (680). The example method of flow diagram 600 further allows the joining of at least two precast segments via at least one interlocking element, such as a bolt or linkage system, or other such slot mechanism, to form a dam at a dam location (681).

Figure 7:
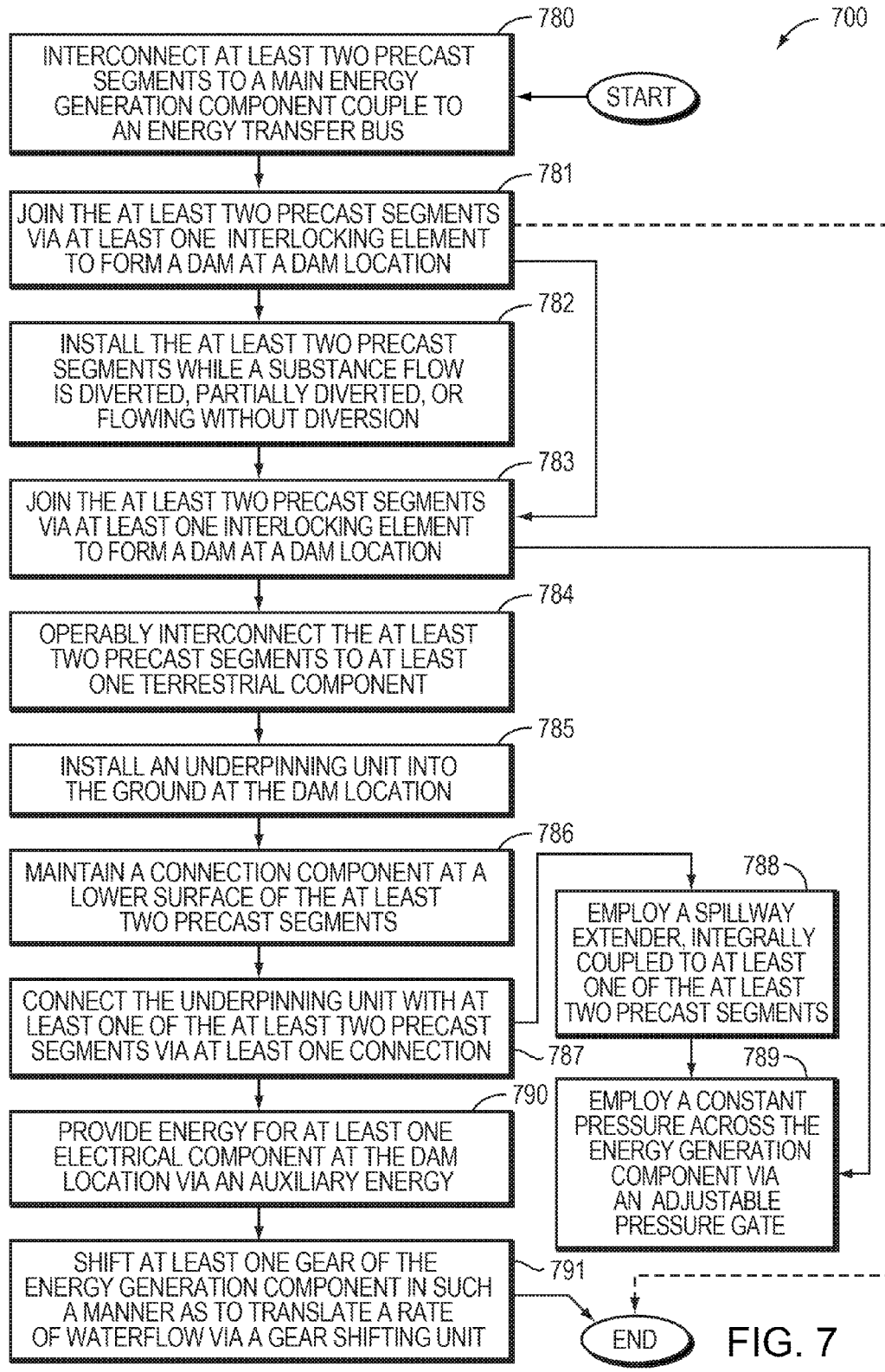
FIG. 7 is a flow diagram of an embodiment of the present invention that illustrates a method of assembling a dam of the present invention.

FIG. 7 is a flow diagram 700 of an embodiment of the present invention that illustrates components involved in assembling a dam of the present invention. After beginning, the method of flow diagram 700 enables interconnecting at least two precast segments to a main energy generation component coupled to an energy transfer bus (780) and joining the precast segments via at least one interlocking element to form a dam at a dam location (781). The method 700 may allow for installing at least two precast segments while a fluid flow is diverted, partially diverted, or flowing without diversion (782) and joining the two precast segments via at least one interlocking element to form a dam at a dam location (783). The method 700 may further allow the precast segments to be operably interconnected to at least one terrestrial component (784) and installing an underpinning unit into the ground or base of a surface at the dam location (785). The method 700 may further be configured to enable the maintaining of a connection component at a lower surface of the precast segments (786). Further, the example method 700 may allow for connecting the underpinning unit with at least one of the precast segments via at least one connection element (787). The method 700 may further enable the employing of a spillway extender, integrally coupled to at least one of the at least two precast segments (788). The method may further provide for a constant pressure across the energy generation component via an adjustable pressure gate (789). Such an example method 700 may enable providing energy for at least one electrical component at the dam location via an auxiliary energy generation component (790) and further allow for shifting at least one gear of the energy generation component in such a manner as to translate a rate of water flow via a gear shifting unit (791). It should be noted that the example method 700 may be performed in alternative manner using a similar or different order of operation as may be seen, for example, in FIG. 7.

A further example embodiment of the present invention can include an existing dam structure, at least two precast segments of the dam configured to be interconnected, and at least one interlocking element or structure configured to join the at least two precast segments to encase the existing dam structure and form the dam at a dam location. Encasing an existing dam structure enables the existing dam structure to be reused as part of the foundation for the (new) dam that can be used to harness hydroelectric power. The precast segments can be arranged to encase the existing dam such that the exposed exterior surfaces of the existing dam are covered and does not necessarily include complete enclosure (e.g., surrounding from all sides including the surfaces of the existing dam which are in contact with soil). Put another way, encasing as used herein with respect to an existing dam does not necessarily mean to fully enclose on all sides, but rather can include leaving the existing dam structure structurally intact in combination with the precast segments of the finished (new) dam. Reusing the existing dam can reduce construction costs by eliminating demolition and removal costs associated with tearing down an old dam. Such reuse can conserve valuable resources.

The precast segments can be further (i) configured to encase and operably interconnect to a main energy generation component configured to convert kinetic energy to an available power, and (ii) coupled to an energy transfer bus.

The available power can be stored at a power supply unit including a battery (or battery system). Further, the available power can be used to power devices, directly or indirectly, operatively coupled to the dam's power generation or storage elements, where the devices may be used to control performance of power generation components, such as the turbine of the dam. In this way, the dam is a self-operating system.

The precast segments can include a composite material that includes electrically conducting fibers, and employ electronics configured to sense strain/stress through use of the electrically conducting fibers. Such a composite material is referred to commonly as smart concrete, such as concrete described in U.S. Pat. No. 5,817,944, entitled "Composite Material Strain/Stress Sensor" by Chung, issued on Oct. 6, 1998, the entire teachings of which are incorporated herein by reference.

An embodiment of the present invention with the precast segments including electrically conducting short fibers can further include insulation membrane on at least non-adjacent faces (e.g., front and back in side-coupling embodiments) to insulate electrical current flowing through the concrete/fibers from exiting via water in a river. The dam can further include a first electric terminal at a first location and a second electric terminal and a second location arranged for measuring electrical resistance as a function of strain/stress between the first and second terminals. Strain/stress as used herein may include multiple strains and/or stresses. The electrically conducting fibers are "short," having respective lengths that are substantially shorter than a distance between the first and second terminals. This enables the stress in the dam to be monitored. The terminals can be arranged on the same precast segment or different precast segments, wherein the case of the other arrangements, multiple adjacent or non-adjacent segments are electrically coupled to enable measurements of segments to be monitored through use of the electrodes. For example, the terminals of multiple precast segments, each having at least two terminals, can be connected in series to form a series sensor to sense the strain/stress applied to the series of precast segments.

An electrical circuit can be used to measure the electrical resistance of the composite material. The electrical circuit can include a transceiver, such as wired, wireless, or optical (free space or fiber), for reporting the measured electrical resistance to a server monitoring the strain/stress on the dam. The electrical circuit can be directly or indirectly powered by the available power generated by the dam and can include a volt meter for measuring the resistance of the composite material (e.g., smart concrete).

An example embodiment of the present invention can further include, a strain/stress signature storage component, such as non-volatile storage medium, to store a representation of a strain/stress signature comprising a strain/stress test output. Such a strain/stress signature storage component allows a baseline strain/stress measurement for future measurements to be compared against, and, therefore, can be used to indicate whether damage or weakening of a dam segment or multiple dam segments has occurred prior to a catastrophic failure. The dam can further include an insulating membrane arranged between the precast segments, formed of an electronically conductive composite material, and an electrically conductive fluid, such as water, obstructed by the formed dam.

The dam can further include (i) a spillway extender integrally coupled to at least one of the precast segments and configured to prevent downstream erosion, (ii) an adjustable pressure gate operably interconnected to at least one precast segment and configured to communicate with an upstream sensor to adjust pressure across the energy generation component and being directly or indirectly powered by the available power, and (iii) a gear shifting unit configured to change at least one gear of the energy generation component in such a manner as to translate a rate of water flow, and being directly or indirectly powered by the available power produced by a turbine at the dam. The gear shifting unit can be self-operating. The spillway extender can be a precast segment.

The dam can further include a drop face wall integrally coupled to and configured with at least one of the two precast segments to encase the existing dam structure. The drop face wall can be a precast segment.

The dam can further include an underpinning unit configured to be installed into the ground at the dam location, a connection component at a lower surface of the at least two precast segments, and at least one connection element configured to connect the underpinning unit with the at least two precast segments. The underpinning unit can be further configured to penetrate through the existing dam structure and be installed into the ground at the dam location on an opposite side of the existing dam structure relative to where the underpinning unit entered the existing dam structure. The connection component can be originally integrated into a lower surface of at least one of the precast segments. Alternatively, the connection component can be configured to be separately coupled to the lower surface of a precast segment.

The precast segments can be configured to be installed either while a fluid (e.g., water) flow is diverted or while a fluid flow is not diverted. The precast segments can be further configured to be operably mechanically or electrically interconnected to at least one terrestrial component.

In a still further example embodiment of the present invention, a dam includes at least two precast segments configured to be interconnected, and at least one interlocking element or structure configured to join the at least two precast segments to encase a main energy generation component and to form the dam at the dam location. The precast segments can be arranged to encase the main energy generation component such that a fluid can flow through the main energy generation component and does not necessarily include complete enclosure (e.g., surrounding from all sides).

A still further example embodiment of the present invention includes a method of assembling a dam at a dam location, including: providing at least two precast segments, joining the at least two precast segments via at least one interlocking element to form the dam at a dam location, and encasing an existing dam structure using the at least two precast segments. The method can further include: encasing and operably interconnecting a main energy generation component with the at least two precast segments, converting kinetic energy to available power using the main energy generation component, and coupling the available power to an energy transfer bus. The method can further include constructing the at least two precast segments using a composite material including electrically conducting short fibers and sensing strain/stress using the composite material.

The method can further include measuring an electrical resistance as a function of strain/stress at a first electrical terminal at a first location of at least one of the at least two precast segments and a second electrical terminal at a second location of at least one of the at least two precast segments. The method can include reporting to a server the electrical resistance using an electrical circuit including a transmitter or transceiver, and powering the electrical circuit with the available power produced by the dam.

The method can further include storing a strain/stress signature comprising a strain/stress test output using a strain/stress signature storage component. Such a storage device enables future strain/stress readings to be compared to a baseline strain/stress signature. The method can further include insulating a fluid obscured by the formed dam from the precast segments using an insulating membrane.

The method can further include: (i) employing a spillway extender integrally coupled to at least one of the at least two precast segments to prevent downstream erosion, (ii) adjusting a pressure across the energy generation component via an adjustable pressure gate, the adjustable pressure gate operably interconnected to a unit or other component of the dam configured to communicate with an upstream sensor, the adjustable pressure gate directly or indirectly powered by the available power produced at the dam, and (iii) shifting at least one gear of the energy generation component in such a manner as to translate a rate of water flow via a gear shifting unit directly or indirectly powered by the available power. The gear shifting unit may perform its shifting in a self-operating manner.

The encasing of the existing dam structure can further include integrally coupling a drop wall face to at least one of the at least two precast segments via at least one interlocking element to encase the existing dam structure and form the dam at the dam location.

The method can further include installing an underpinning unit into the ground at the dam location, maintaining a connection component at a lower surface of the at least two precast segments, and connecting the underpinning unit with at least one of the at least two precast segments via at least one connection element. The installing of the underpinning unit into the ground at the dam location can further include penetrating the existing dam structure with the underpinning unit. The connection component can be originally integrated, or separately coupled to, the lower surface of at least one of the at least two precast segments. Installing the at least two precast segments can be done while a fluid is diverted, partially diverted, or flowing without diversion. The method can further include operably interconnecting at least two precast segments to at least one terrestrial component. The method can further include energizing at least one electrical component at the dam via an auxiliary generation component.

A still further embodiment of the present invention includes a method of assembling a dam at a dam location, the method comprising providing at least two precast segments and joining the at least two precast segments via at least one interlocking element to encase a main energy generation component and form the dam at the dam location.

Still further embodiments of the present invention can include means for encasing an existing dam structure and forming a structure of a dam and means for interlocking said means for encasing and forming the structure of the dam.

A still further example embodiment of the present invention can include means for forming a structure of a dam and encasing a main energy generation component, and means for interlocking said means for encasing and forming the structure of the dam.

Figure 8:
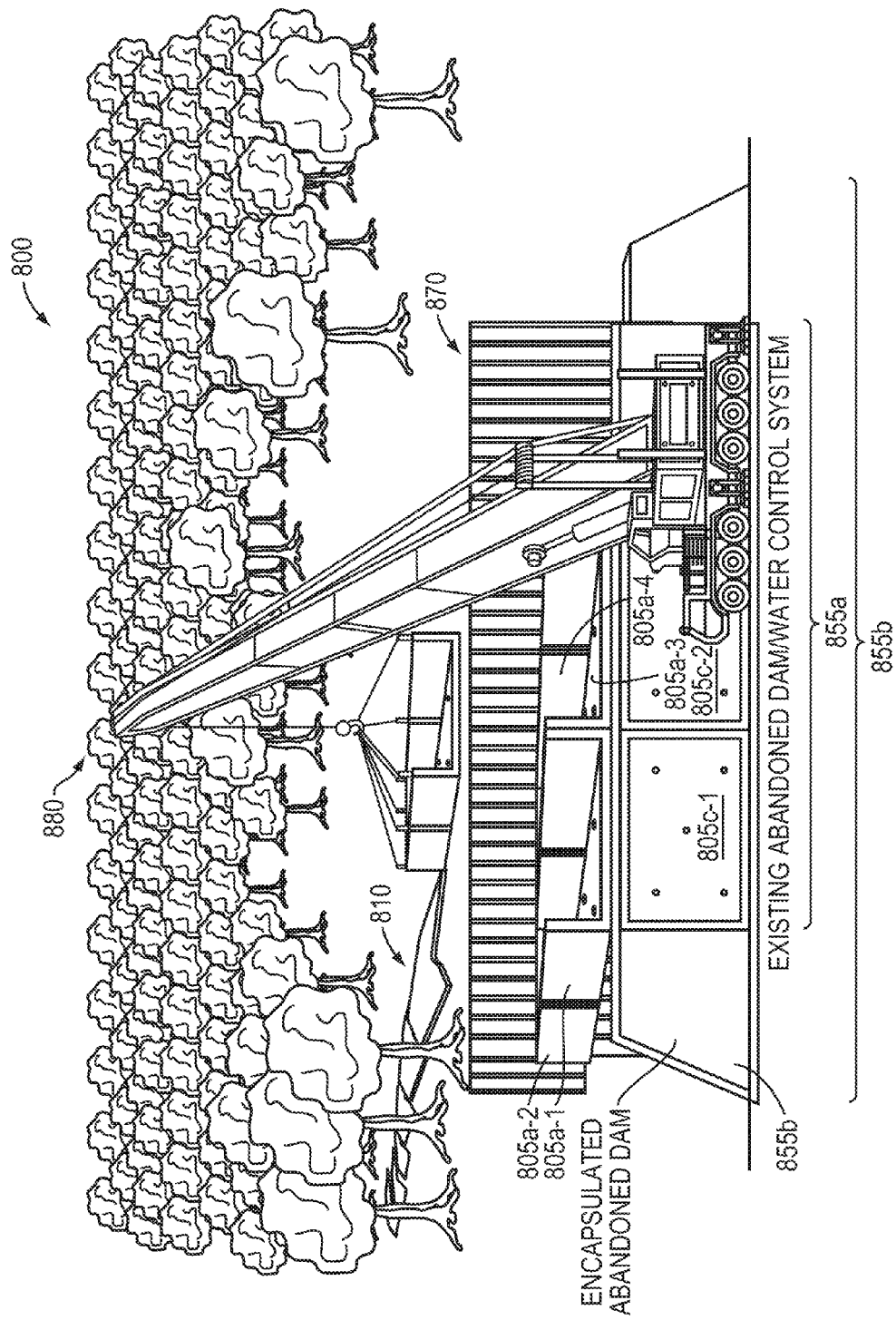
FIG. 8 is a diagram of an environment in which example embodiments according to the present invention may be employed.

FIG. 8 is a high-level diagram 800 of an environment in which example embodiments according to the present invention may be employed, and includes an existing dam 855*b*, segmented precast segments 805*a*-1 . . . 5, 805*c*-1, 2, cofferdam system 870, and installation equipment 880.

The cofferdam system 870 can be used to divert water flow from a river 810 temporarily while a dam 855*a* is constructed according to an example embodiment of the present invention. The existing dam structure 855*b* can be encased (or encapsulated) using precast segments 805*a*-1 . . . 805*c*-2 according to an embodiment of the present invention. By encasing the existing dam with precast segments, construction costs are reduced due to the fact that the existing dam does not need to be demolished and removed. Further, the precast segments 805*a*-1 . . . 5 enable construction to be quick, easy, and efficient since the precast segments can be manufactured off-site and deployed to the construction site using conventional logistic techniques, such as typical tractor trailers. As shown in the diagram 800, the precast segments can be used to encase the existing dam and construct the (new) dam by installing precast segments, such as by starting from the lowest elevation and working upwards by interconnecting the precast segments. As shown in the example diagram 800, the installed drop face wall precast segments 805*c*-1, 2 are installed first, and precast segments 805*a*-1 . . . 5 are then installed and interconnected to respective drop face walls 805*c*-1, 2. The interconnection can be performed using an interlocking element or structure configured to join the precast segments, such as keyways and bolt linkage systems, or any other method described herein.

Figure 9:
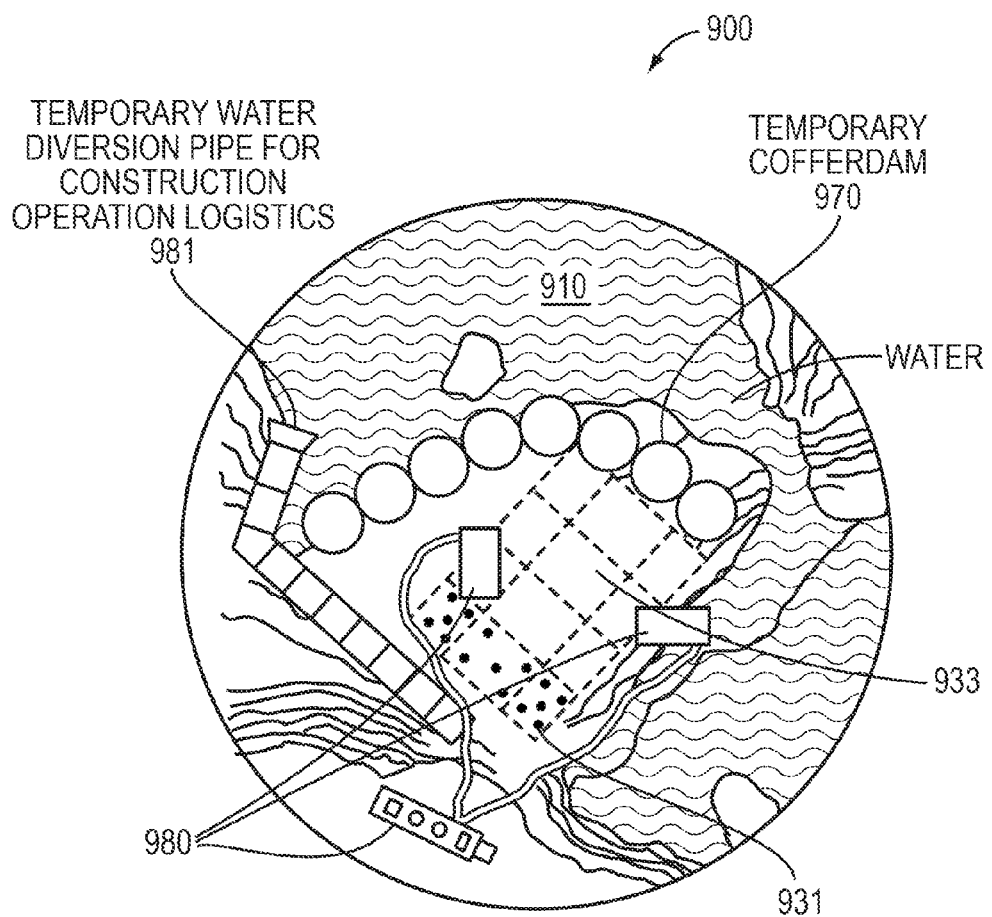
FIG. 9 is a bird's eye view of an installation's construction site according to an embodiment of the present invention.

FIG. 9 is a bird's eye view 900 of an installation's construction site according to an embodiment of the present invention. The bird's eye view 900 of the construction site includes a waterway 910 being diverted by a temporary cofferdam 970, heavy construction equipment 980, temporary water diversion pipe 981 for construction operation logistics, and underpinning installation site locations 931. The dashed lines 933 indicate the installation locations for precast segments. The sighting for the underpinning units 931 can be performed using a GPS system to ensure an accurate and precise layout, ensuring adherence to engineering plans.

Figure 10:
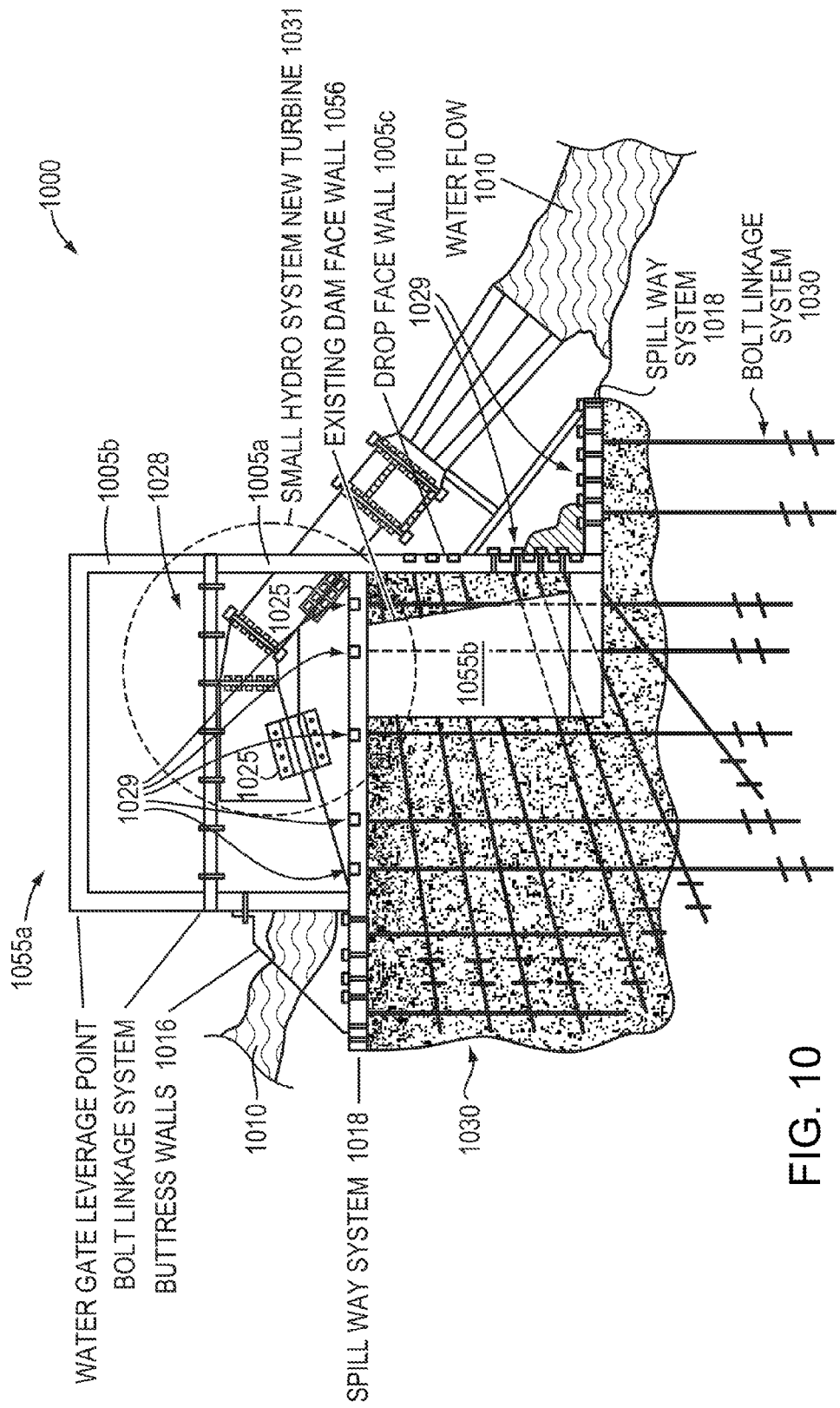
FIG. 10 is a side cutaway view of a dam according to an embodiment of the present invention.

FIG. 10 is a side cutaway view 1000 of a dam 1055*a* according to an embodiment of the present invention. The side cutaway view 1000 includes the dam 1055*a*, existing dam structure 1055*b*, water flow 1010, precast segments 1005*a*-*c*, spillway system 1018, buttress walls 1016, underpinning units 1030 (collectively referred to as an underpinning system), connection components and elements 1029, keyway and bolt linkage system 1028, small main energy generation component 1031, and bolt linkage system 1025.

According to an embodiment of the present invention, the existing dam structure 1055*b* is encased within the dam 1055*a*, where the precast segments 1005*a*-*c* of the dam 1055*a* are used to encase the existing dam structure 1055*b*. Precast segments 1005*a*-*c* can be interconnecting and interlocking and can use interlocking elements or structures configured to join the precast segments to encase the existing dam structure 1055*b* and, thus, form the dam 1055*a*. The drop face wall 1005*c* can be installed on, or in front of, the face wall 1056 of the existing dam structure 1055*b*. The space behind the exterior of the drop face wall 1055*c* between the drop face wall 1055*c* and the face wall 1056 of the existing dam structure 1055*b* (if any exists) can be filled with a fill material, such as mortar, grout, or any other fill suitable to provide stability and support to the drop face wall 1005*c* and dam 1055*a*.

The drop face wall 1005*c* can have keyway interconnecting segments and interconnecting elements or structures, as will be described in more detail below. Drop face wall 1005*c* can be integrally connected or can be integrally coupled to and configured with the precast segments 1005a-c to encase the existing dam structure and form the dam 1055a. Precast segment 1005a can be used to help encase not only the existing dam 1055b, but also to encase the main energy generation component 1031 (for example, a small head hydroelectric system). Precast segment 1005b can be used with precast segment 1005a to encase (enclose or encapsulate) main energy generation component 1031. Precast segments 1005a, b can be configured to interconnect with each other using at least one interlocking element or structure, such as a bolt linkage system 1028.

The main energy generation component 1031 can be coupled to the precast segments 1005a, b using bolt linkage systems 1025. Such a bolt linkage system 1025 can be, for example, a bracket and bolt system. Precast segments 1005a, b can be designed to accommodate main energy generation components, such as small head hydroelectric systems manufactured by different manufacturers and in different sizes, configurations and shapes. The ability to customize the shapes and dimensions of the precast segments 1005a-c allows the dam 1055a to use hydroelectric systems produced by various manufacturers and to accommodate various different water flow environments.

The precast segments 1005a-c, spillway extender 1018, and buttress walls 1016 can be installed at a site using underpinning units 1030. The underpinning units 1030 can be also referred to as "soil nails" or "earth screws" and used to stabilize the segmented dam 1055a by creating a stable coupling to the earth (e.g., stable soil, riverbed or bedrock) beneath the existing dam structure 1055b. The underpinning units can penetrate through the existing dam 1055b in order to create a stable foundation for the new dam 1055a. The installation points of the underpinning units can be sited using a GPS system. The installation points can be drilled out to form pre-drilled holes to accept the underpinning units 1030. The underpinning units 1030 can be used to create an in-situ reinforcement system (e.g., the underpinning system) to stabilize construction of the new dam 1055a. The underpinning units 1030 can be made up of underpinning components. The underpinning components may include a centralized component, and one or more centralizers, as well as a fill (or grouting material) surrounding the centralized component and/or one or more centralizers. The centralized component can be a metal cylindrical component having a length much greater than its diameter, for example, threaded rebar, and inserted into the pre-drilled holes. The centralizers can be a fastener or expansion anchor having a central hole, which can be threaded and used to couple to the centralized component. The fill or grouting material, such as concrete or other composite material, can be pumped into the pre-drilled holes with the inserted underpinning components.

Connection elements 1029b can be coupled to, or integrated with, the underpinning units 1030 at an end opposite of the end that is first inserted into the pre-drill hole. For example, the connection element 1029b may be a threaded bolt having one end coupled to the underpinning unit 1030. Connection components 1029a can couple to the connection elements 1029b. For example, the connection components 1029a may include a washer and nut and be used to connect the precast segments 1005a, c to the underpinning units 1030. The precast segments 1005a, can be performed with a linkage points 1029c (e.g., receptacles or pass-through openings) to accommodate the connections elements 1029b and/or underpinning units 1030. Alternatively, the linkage points 1029c of precast segments 1005a,c can be formed on site, using a drill or other similar method. Further, the precast segments 1005a,c can have linkage points 1029c preinstalled with connection elements 1029b and/or connection components 1029a.

FIGS. 11A-11C illustrate various views of precast segments.

FIG. 11A illustrates a side view of precast segments 1105a and 1105b from a perspective of a viewer looking into (or from) the dammed body of water. Precast segments 1105a,b can be used to encase (or encapsulate) the main energy generation component (not shown in FIG. 11A) with an interior cavity of the interlocked interconnected precast segments. The interior cavity can be cylindrical, rectangular, or any other appropriate shape. The precast segments 1105a,b include a bolt linkage system 1125 that can be used to couple the main energy generation component to the precast segments 1105a,b.

It should be understood by those of skill in the art that the precast segments 1105a,b including their interiors, can be of various shapes and sizes, in order to accommodate the different shapes and sizes of main energy generation components, such as small head hydroelectric systems manufactured by various manufacturers. As such, the semicircular shape of 1105a,b can also be rectangular or any other suitable shape.

The precast segments 1105a,b can also include two-way and interlocking keyway elements or structures 1171 configured to ensure that the precast segments can be installed only in a designed orientation during on-site installation. The keyway elements or structures 1171 can include male and female keyways. The precast segments 1105a,b can further include interlocking elements 1128a,b. Such interlocking elements or structures 1128a,b can be configured to join the precast segments to encase the existing dam structure and form the dam. The interlocking elements 1128a,b can include bolt linkage systems and/or keyway systems.

FIG. 11B is a bottom view of a precast segment 1105b. The keyway interconnecting features 1171 and interlocking element or structure 1128a are shown. The black shading of the interlocking element or structure 1128a and interconnection features 1171 indicates that the interlocking elements are male and extend out of the page. These interlocking elements or structures are coupled to corresponding female elements, as shown in FIG. 11C, where the female elements are shown in white fill.

FIG. 11C illustrates a top view of the precast segments 1105a and includes interconnecting elements 1171 and 1128b. The keyway interconnecting features 1171, and interlocking element or structure 1128b are shown. The white shading of 1128a and 1171 indicates that the interlocking elements are female and sink into the page. These interlocking elements or structures 1128a and 1171 are coupled to the corresponding male elements, as shown in FIG. 11B, during assembly of the dam.

The precast segment 1105a may include connection elements 1129a, 1129b, and linkage point 1129c, connection components at a lower surface of the precast segment 1105a, which connects to an underpinning unit 1130 in order to secure the precast segment 1105a to the underpinning unit 1030. By securing the precast segments 1105a, movement of the precast segments 1105a due to forces applied by water flow does not occur. Other precast segments not directly connected to the underpinning units 1130, such as precast segment 1105b, are secured to the underpinning units 1030 by way of the interconnected and interlocking elements 1128a,b.

Figure 12B:
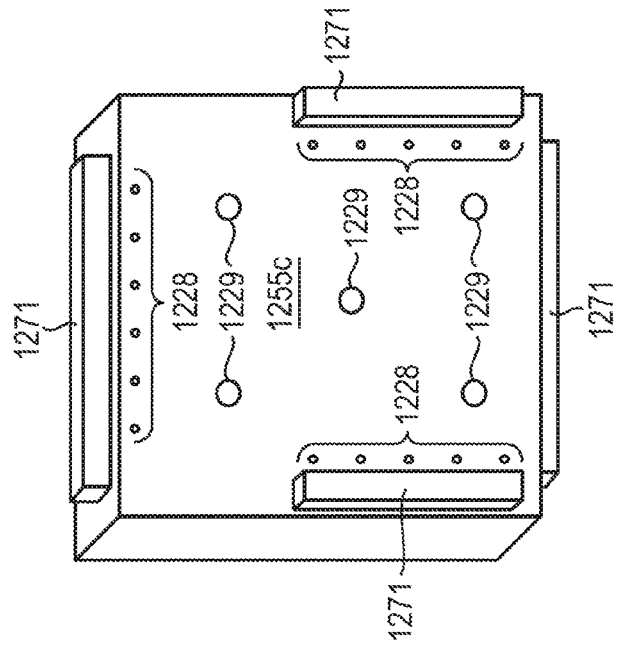
FIGS. 12A and 12B illustrate a drop face wall precast segment.
Figure 12A:
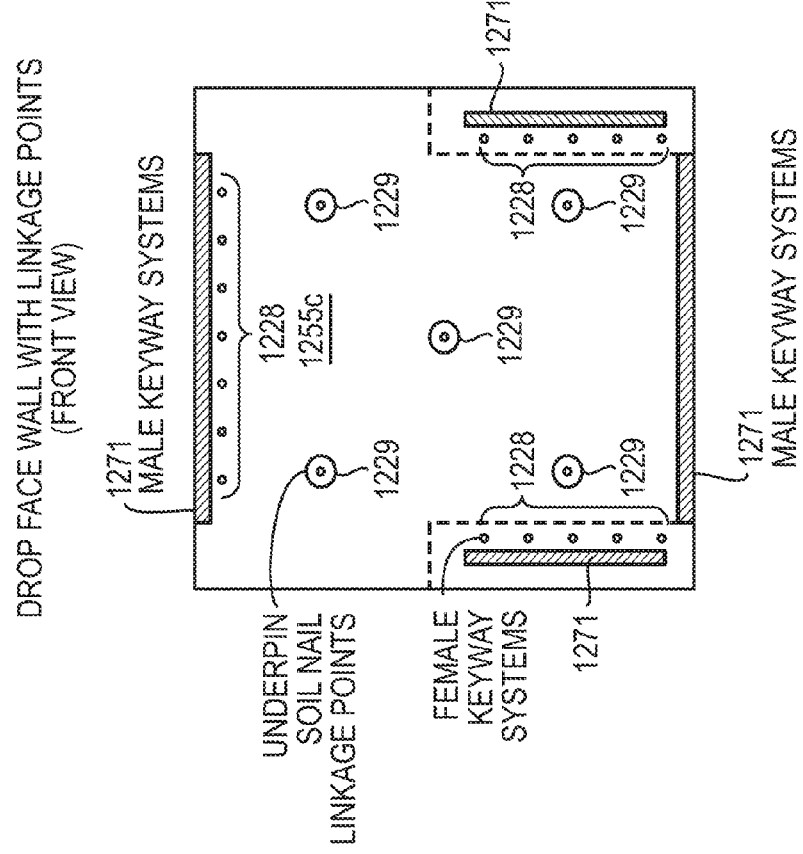

FIGS. 12A and 12B show a drop face wall precast segment 1205c from a front view and perspective view, respectively. The drop face wall 1205c includes keyway systems 1271 (e.g., male or female features, structures, or elements) interconnecting and interlocking elements or structures 1228, such as a bolt linkage system, and connection components 1229.

Figure 13:
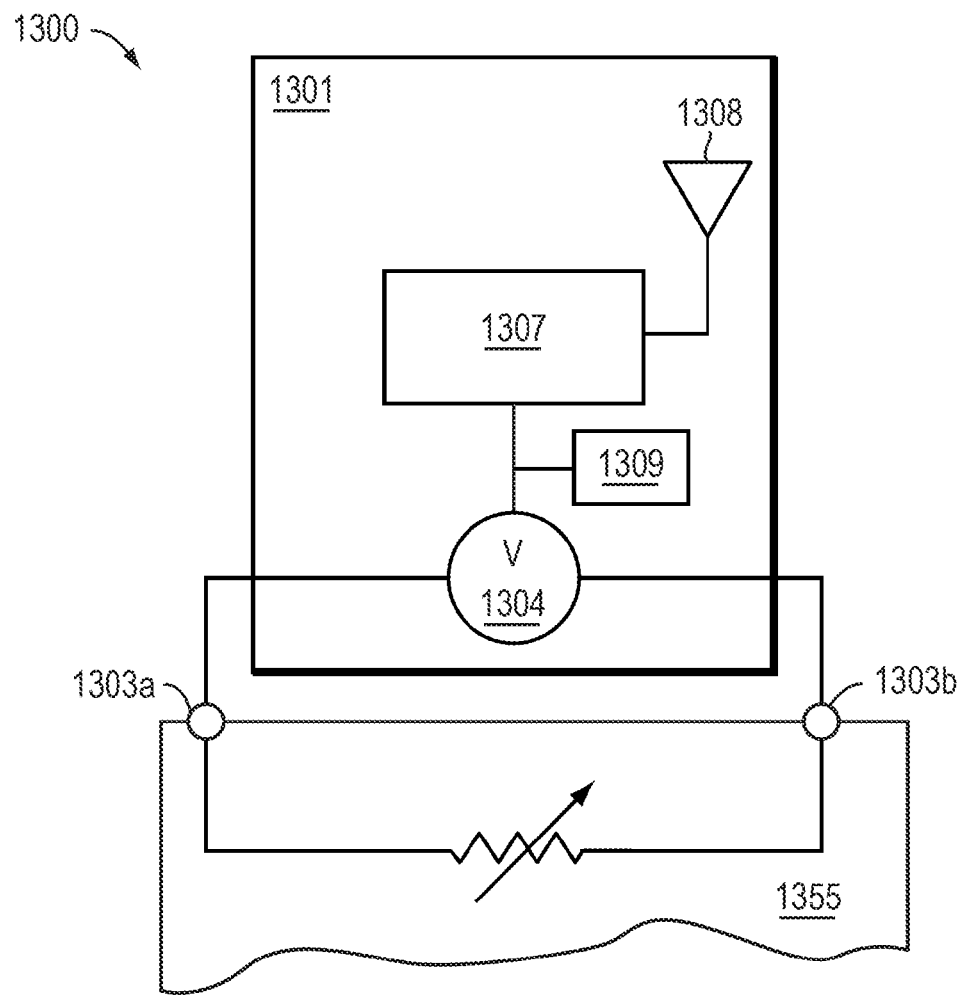
FIG. 13 is a schematic diagram of an electrical circuit including a strain/stress sensor according to an embodiment of the present invention.

FIG. 13 is a schematic diagram of an electrical circuit 1300 that may be employed with an embodiment of a dam. The electrical circuit 1300 includes an electrical circuit structure 1301, first and second electric terminals 1303a and 1303b, respectively, and strain/stress sensor 1305. The strain/stress sensor 1305 can be a precast segment made from a composite material including electrically conducting short fibers (e.g., fibers that do not individually span between the terminals 1303a, 1303b and configured to sense strain/stress after construction of the segment, including after assembly of the dam and during use of the dam. One such composite material strain/stress sensor is disclosed in U.S. Pat. No. 5,817,944 entitled "Composite Material Strain/Stress Sensor" by Chung, issued Oct. 6, 1998.

The precast segments 1305 can be made from a composite material containing electrically conducting fibers having a somewhat conductive matrix. An increase in crack concentration or size causes an increase in the amount of fiber pullout, resulting in an increase in the electrical resistance, which is the measured response to the strain/stress stimulus. Composite materials, such as concrete, are somewhat electrically conducting, and so can be used in combination with electrically conducting fibers to form a stress/strain sensor. Further, cracking under stress/strain can be detected and controlled rather than being allowed to occur catastrophically according to an embodiment of the invention. Monitoring of such sensing is useful for dams as the monitoring and sensing increases safety and allows for damage to be repaired before a catastrophic failure occurs. Also, the electrically conducting short fibers can be much more conductive in the composite material matrix, so that the fibers contribute to the electrical conductivity of the material.

The electrical circuit 1300 can further include, within the electrical circuit structure 1301, a voltmeter 1304 to measure the resistivity (or conductivity) of the composite material sensor 1305 between the first terminal 1303a and the second terminal 1303b. The conductivity measured by the voltmeter 1304 can be communicated to a transceiver 1307 and broadcast or transmitted, via an antenna 1308, to a remote server (not shown), which can be located remotely, and used to monitor the measured resistivity of multiple dams and multiple segments of the multiple dams. Also, the transceiver 1307 can have an ability to communicate over a wired (or optical) channel. The transceiver 1307 can receive inputs from multiple voltmeters and transmit multiple measurement readings to the remote server.

The electrical circuit 1300 can further include a strain/stress signature storage component 1309. The strain/stress signature storage component 1309 can store a strain/stress signature, which can be a strain/stress test output. Such a strain/stress test output can be the result of measuring the resistivity (or conductivity) of the composite material 1305 at a precast factory point of manufacture (e.g., a quality assurance step in the manufacturing process to establish a "baseline factory measurement" for strain/stress). The precast strain/stress signature can be stored using any known method, such as machine-readable non-volatile RAM, RFID, memory card, etc., or 2-D matrix barcode, or alternatively using human-readable forms. Using such a factory calibration to record the original strain/stress signature of the composite material 1305, the strain or stress readings can be measured after installation and during the life of the dam and compared to the factory measurement, thus any changes from the initial manufacturing baseline measurement can be detected easily.

The electrical circuit 1300 can be powered using the available power converted from kinetic energy by the main energy generation component at the dam. Such available power may be stored on site in a battery, series of batteries, or battery system, thereby enabling the electrical components of the electrical circuit 1300 to be powered, and for the stress/strain to be sensed using the stress/strain sensor 1305.

Further, control software can be implemented to control the gate pressure for water entering the feed for the main energy generation components based on sensors upstream. Communication with the sensors upstream, whether wired, wireless, or optical, can be powered by the available power either direct or indirectly as generated by the main energy generation component.

An example process for installing a dam in accordance with the inventive principles disclosed herein follows. It should be understood by those of skill in the art that the procedure may be performed in any order, and will likely be dictated by site factors, including, but not limited to, the existing dam structure, the body of water and/or associated water flow, construction schedule, logistics, and availability of materials, and environment surrounding the site. For example, a coffer dam is installed to divert part or all of a flowing fluid, such as a river, at a site of an existing dam structure. Next, the site is prepared for construction of the dam (e.g., installation of precast segments) through the clearing of any unsuitable soil materials, such as large rocks. After the site has been cleared appropriately, the installation points for the underpinning units can be sited (using GPS) and marked for drilling. The installation points can then be drilled out to form pre-drilled holes to accept the underpinning units. The underpinning units can then be installed and may, optionally, penetrate the existing dam structure.

Next, precast segments are installed. For example, installation can begin at the point of lowest elevation with installation of the drop face wall segments. Installation of the drop face wall segments can include connecting connection components to the underpinning units to secure the drop face wall segments. Any cavities that may be formed between the existing dam structure and the installed drop face wall segments can be filled using a fill material suitable to provide stabilization and structure. Additional drop dace wall segments can then be installed in a similar manner and interconnected to each other using interlocking elements or structures. The interconnected drop wall segments may be configured in an arrangement that not only transverses the length of the existing dam structure, but also builds upwards.

Upon completing the installation of the drop wall face segments, the precast segments may be installed along the topside of the existing dame structure. For example, installation of the precast segments can begin at the junction with the drop face wall or the point of lowest elevation. Installation of the precast segments can include connecting connection components to the underpinning units to secure the drop face wall segments. Any cavities that may be formed between the existing dam structure and the installed precast segments can be filled using a fill material suitable to provide stabilization and structure. The installation of the precast segments can be performed similar to the installation of tiles, for example, starting with a first row and installing the next precast segments in order to transverse across the existing dam structure, then installing a next row in the same manner. As part of the installation, the face wall can be integrally coupled (or interconnected) to the precast segments using interlocking elements or structures to join the drop face wall segments and the precast segments.

After the first precast segments are installed, main energy generation components, such as hydroelectric generator, are placed within a cavity, (bed or compartment) provided by the precast segments. Next, the main energy generation components are mechanically coupled to the precast segments, for example using bolt linkage system such as brackets and bolts.

Once the main energy generation components are installed, the second precast segments are installed. Installation of the second precast segments may be performed in a manner similar to that described above with respect to the first precast segments. Installation of the second precast segments, encases the main energy generation components; a main energy generation component is sandwiched between at least two precast segments. The second precast segments are interconnected to respective first precast segments using at least one interlocking element or feature, such as a bolt linkage and/or keyway. First and second precast segments are also interconnected to adjacent first and second precast segments using at least one interlocking element or feature, such as a bolt linkage and/or keyway. Next, spillways can be installed to prevent erosion. Buttress walls can be installed for additional structural support and to facilitate the flow of fluid.

Although not illustrated in detail in the figures, a structure that houses storage elements, such as batteries, may be constructed, optionally with precast elements, at the site of the dam or a short distance away, with energy generated by energy generating devices at or within the dam to be connected to the energy storage devices via electrical cables or other power transfer means.

Further, although not illustrated in the diagrams, any form of controller, such as general-purpose microprocessor, signal processor, hardware, software, or other elements that may be used to control electro-mechanical elements, may be employed to operate any of the electro-mechanical elements described herein.

Other example embodiments of the present invention may include a non-transitory computer readable medium containing instruction that may be executed by a processor, and, when executed, cause the processor to perform different functions, for example, to change the height of the gate used to control water height or flow, change the gear ratio of gears coupled to a water wheel or turbine, or even control any electrical elements associated with energy transfer to the energy storage elements or to the energy grid to which energy is or may be transferred. It should be understood that elements of the block and flow diagrams described herein may be implemented in software, hardware, firmware, or other similar implementation determined in the future. In addition, the elements of the block and flow diagrams described herein may be combined or divided in any manner in software, hardware, or firmware. If implemented in software, the software may be written in any language that may support the example embodiments disclosed herein. The software may be stored in any form of computer readable medium, such as random access memory (RAM), read only memory (ROM), compact disk read only memory (CD-ROM), and so forth. In operation, a general purpose or application specific processor loads and executes software in a manner well understood in the art. It should be understood further that the block and flow diagrams may include more or fewer elements, be arranged or oriented differently, or be represented differently. It should be understood that implementation may dictate the block, flow, and/or network diagrams and the number of block and flow diagrams illustrating the execution of embodiments of the invention.

Further, any form of solar paneling may be employed, including solar trackers and any other auxiliary power systems may be employed to provide the energy, or backup of energy, for operating the electronics that may be associated with the dam, as disclosed herein.

Figures 1, 14A:
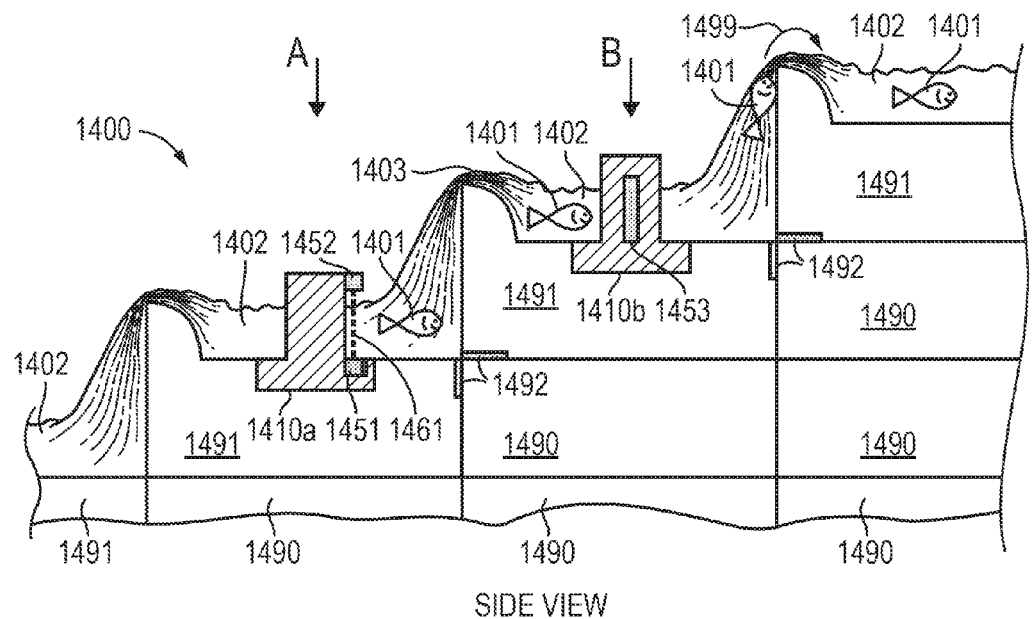
FIG. 14A-1 is an illustration of an aquatic animal passage system including chutes constructed from precast cement segments and devices for counting animal traffic.

FIGS. 14A1, 14A-2, and 14B are illustrations of an aquatic animal passage system including chutes constructed from precast cement segments and a device for counting animal traffic. FIG. 14A-1 shows an aquatic animal passage system 1400, which may be, for example, a fish ladder, having a series of stepped pools of water 1402 formed by a series of dams 1403, or an eel passageway. Typically, aquatic animal passage systems 1400 are artificial structures positioned near or around waterway barriers, such as dams or locks, to enable aquatic wildlife to travel upstream and downstream of the barrier, usually through a series of low stepped pools having a reduced velocity of water flowing between them. The eel passageway may be in a geometry of a slope ascending from downstream to upstream and formed by a precast segment optionally coated with a non-abrasive coating. The eel passageway may have special surface features that eels push against as they move upstream on the passageway against a current. The eel passageway may alternatively be formed of a planar structure, such as fiberglass, that provides the surface features. The planar structure may be coupled to a precast cement segment or other structure or riverbed in a static manner, such as by way of connections by metal bolts. It should be understood that eel passageways may be shaped as tubes, partial tubes or shape.

In the example aquatic animal passage system 1400, the series of stepped pools of water 1402 enable fish 1401 to travel upstream by jumping over the series of dams 1403 (as indicated by an arrow 1499) or swimming up a short waterfall flow between the stepped pools 1402. The aquatic animal passage system 1400 may be constructed from a plurality of precast concrete segments, for example, pool sections 1491 placed atop base sections 1490, thereby providing a step-formation to enable water 1402 to flow between each of the pool sections 1491. The precast concrete segments 1490, 1491 may include a plurality of joining-features (not shown) to couple each precast segment 1490, 1491 to its surrounding segment 1490, 1491 or to an adjacent structure, such as a preexisting dam (not shown). Additionally, sealing members 1492, such as rubber composite, or cementitious material, may be placed between the pool sections 1491 and the base sections 1490 to prevent water 1402 from flowing between the precast concrete sections 1490, 1491, and a hydrophobic coating or liner (not shown) may be coupled to the outer surface of the pool section 1491 to protect aquatic animals traversing the aquatic animal passage system 1400 and to help seal the segments 1490, 1491 to limit waterflow and ice formation in gaps therebetween.

Figure 14B:
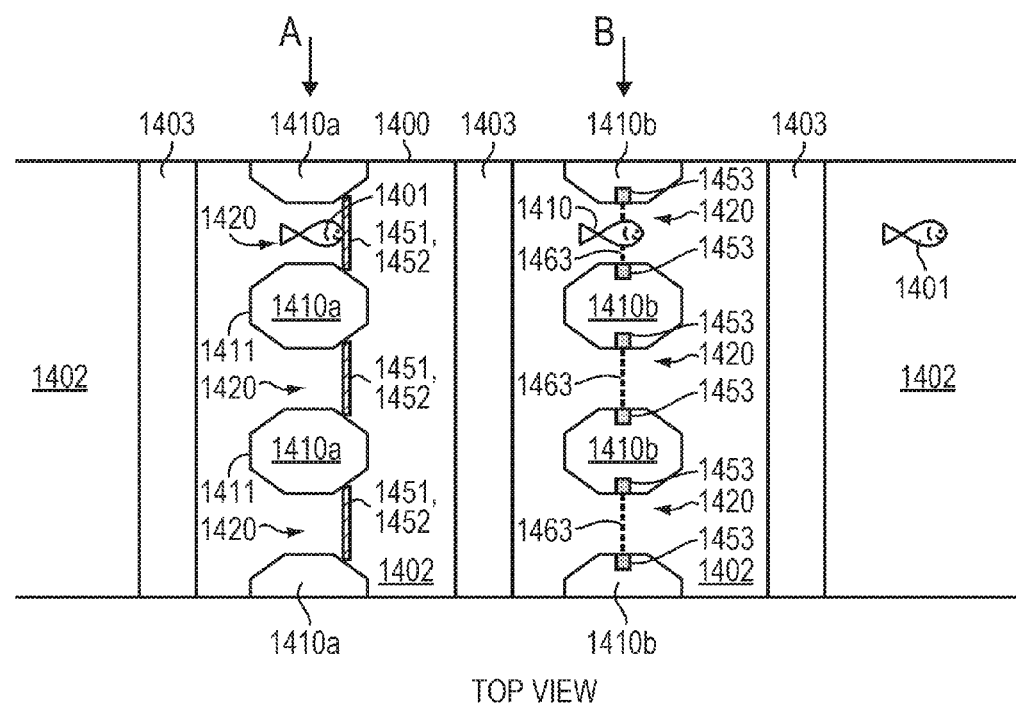
FIG. 14B is top-view illustration of the aquatic animal passage system of FIG. 14A-1.
Figures 2, 14A:
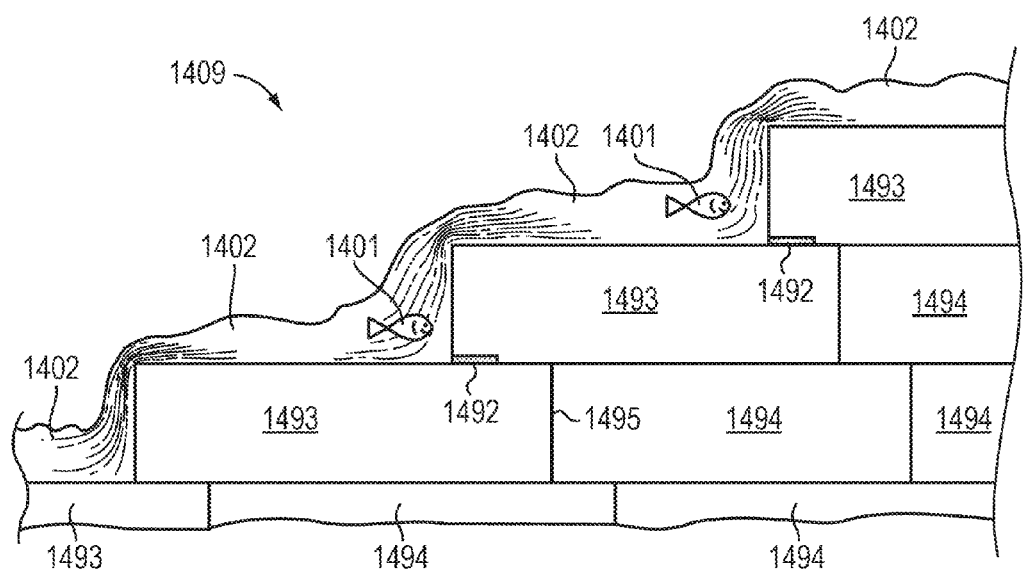

An alternative aquatic animal passage system 1409 is shown in FIG. 14A-2, with elongated pool sections 1493 coupled with elongated precast base members 1494 arranged to offset the joints 1495 or gaps between the elongated precast concrete sections 1493, 1494. The configuration shown in FIG. 14A-2 enables fewer sealing members 1492 to be needed to seal the elongated pool section 1493 and, by eliminating the continuous, aligned, inter-segment interface gaps and joints present in the configuration of FIG. 14A-1, the structural integrity of the aquatic animal passage system 1409 may be increased. It should be noted that in many embodiments of the aquatic animal system 1400, 1409, adjacent segments may include complimentary features (e.g., protrusions and sockets of inversely-matching geometrical shapes) to provide close coupling and strength between the corresponding adjacent segments for overall structural integrity of the passage system 1409. Coupling mechanisms, such as metal strappings known in the art, may also be employed.

Referring again to FIG. 14A-1, to quantify and monitor the effectiveness of the aquatic animal passage system 1400, a fish-counting device may be incorporated into, or very close to, the stepped pools of water 1402 to enable detection and reporting or recording of the quantity or volume of animal traffic through the aquatic animal passage system 1400.

One such fish-counting device is shown in FIGS. 14A-1 and 14B, side view and top view, respectively, and may be incorporated into the structure of the aquatic animal passage system 1400. Referring to FIGS. 14A-1 and 14B, to count individual fish easily and accurately, a series of chutes 1420 may be incorporated into one or more of the stepped pools of water 1402 along with sensors positioned to detect animals, such as fish 1401, moving through the chutes 1420. The chutes 1420 may be any aquatic passage or opening in the aquatic animal passage system 1400 though which animals may pass. The chutes 1420 may be constructed from one or more pre-cast concrete segments 1410 placed in at least one of the stepped pools of water 1402 and lined with a protective liner 1411 or coating to protect fish 1401 as they swim upstream through the chutes 1420. Different types of sensors may be positioned in or near the chutes 1420 to detected fish 1401 traffic. For example, vertical sensors 1451, 1452 may be positioned above and below each chute 1420 to create a vertical sensing region 1461 (between the pre-cast concrete segments 1410*a* shown as column "A"), or horizontal sensors 1453 may be positioned on one or more sides of the pre-cast concrete segments 1410*a* forming the chutes 1420 to create a horizontal sensing region 1463 (between the pre-cast concrete segments 1410*b* shown as column "B").

Additionally, any of the sensors may be integrated into the pre-cast concrete segments 1410*a*. For example, column "B" shows a series of pre-cast concrete segments 1410*b* having integrated horizontal sensors 1453. Sensors being integrated into the pre-cast concrete segments may be positioned, for example, in (i) voids (not shown) in the pre-cast concrete segments 1410*b* shaped to accept a sensor or sensor module, (ii) passages (not shown) in the pre-cast concrete segments 1410*b* positioned to facilitate installing a sensor in the pre-cast concrete segments 1410*b*, or (iii) pockets in or on the pre-cast concrete segments 1410*b* during casting of the pre-cast concrete segments 1410*b*. The vertical sensors 1451, 1452 and horizontal sensors 1453 may be, for example, simple optical counters or photographic sensors. Alternatively, or in additional to the vertical sensors 1451, 1452 and horizontal sensors 1453, other sensors (not shown) using alternative sensing techniques well known by those skilled in the art may be used. For example, impedance-type counters configured to measure a disturbance in an electric field when a fish 1401 passes through the chutes 1420, or hydroacoustic counters using sonar, may be used to detect and locate the passage of fish 1401 through the chutes 1420 between the pre-cast concrete segments 1410*a*. In one embodiment, the pre-cast concrete segments 1410*a* are constructed from smart concrete (described above), and an electric field of an impedance-type counter is created by applying current into one or more of the pre-cast smart concrete segments 1410*a*. Thus, smart pre-cast segments can be used as transducers within a fish sensor.

Figure 15:
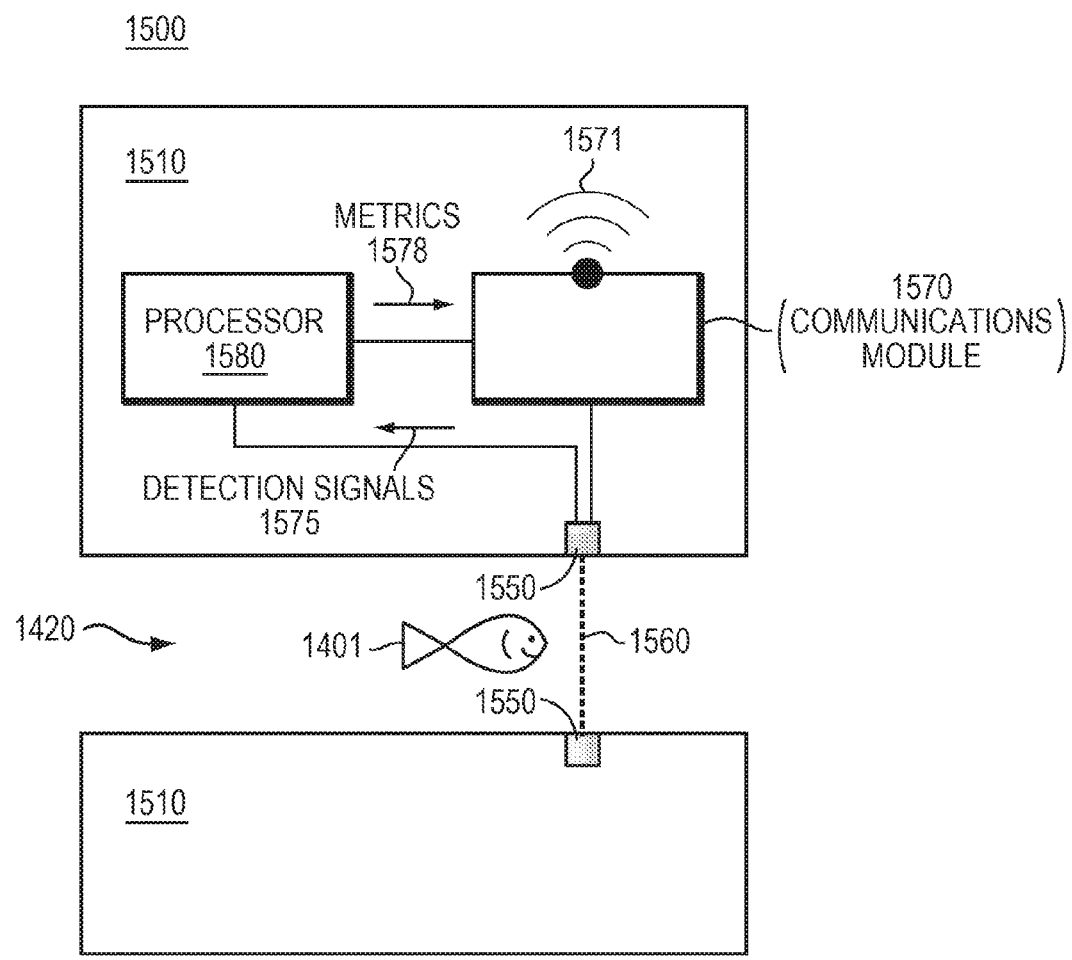
FIG. 15 is a schematic illustration of a device for counting animal traffic through chutes in an aquatic animal passage system.

FIG. 15 is a top view schematic illustration of a device for counting animal traffic through chutes in an aquatic animal passage system. FIG. 15 shows a fish counter 1500 having a chute 1420 formed with pre-cast segments 1510. The fish counter 1500 includes sensors 1550 forming a sensing region 1560 between the pre-cast segments 1510. The sensors 1550 are configured to detect the passage of aquatic life, for example, fish 1401, passing through the sensing region 1560. The sensors 1550 may be configured to sense, for example, the direction of fish 1401 moving through the chute 1420, the number of individual fish 1401 in or moving through the chute 1420, or the volume of fish 1401 in or moving through the chute 1420. The sensors 1550 may be operatively coupled with a communications module 1570 integrated with the sensor 1550 or located in an adjacent pre-cast segment 1510. The communications module 1570 may alternatively be an external communications device.

Additionally, the fish counter 1500 may be operatively coupled to a local (or remote) processor 1580 configured to accept a detection signal and calculate, for example, the direction of fish 1401 moving in the chute 1420, the number of individual fish 1401 moving through the chute 1420, or the volume of fish 1401 in the chute 1420. In the embodiment of FIG. 15, the sensors 1550 may be connected to the processor 1580 directly or through the communications module 1570 through a wired, wireless 1571, or optical connection. The communications module 1570 and processor 1580 may be configured to receive and record a detection signal 1575 from one or more sensors 1550 and may be further configured to connect wirelessly 1571 with external devices (not shown) to transmit the metrics 1578 calculated by the processor 1580. The metrics 1578 may be stored externally and presented to a conservation authority tasked with tracking aquatic animal counts and aquatic animal travel schedules.

While this invention has been particularly shown and described with references to example embodiments thereof, it will be understood by those skilled in the art that various changes in form and details may be made therein without departing from the scope of the invention encompassed by the appended claims.

What is claimed is:

1. A device for counting animal traffic in an aquatic animal passage system, the device comprising:
   one or more chutes positioned across the aquatic animal passage system, the one or more chutes and the aquatic animal passage system being formed with precast concrete segments, the precast concrete segments adapted to interconnect with adjacent precast concrete segments and including at least base sections and top sections, the top sections defining a waterway of the aquatic animal passage system, wherein the aquatic animal passage system includes at least two horizontal rows of base sections, each base section being horizontally offset from at least one vertically adjacent base section; and
   one or more sensors positioned to sense an animal in the aquatic animal passage system, the one or more sensors being responsive to animals moving through the one or more chutes and adapted to sense at least one of: a number of animals and a volume of animals traveling through the aquatic animal passage system.

2. The device of claim 1, further including:
   a protective liner or coating coupled to a surface of the one or more chutes, the protective liner or coating protecting animals in the one or more chutes from contacting an outer surface of the precast concrete segments forming the chutes.

3. The device of claim 1, wherein the one or more sensors are integrated with the precast concrete segments forming the one or more chutes.

4. The device of claim 1, wherein the one or more sensors include at least one of the following: an optical sensor, a photographic sensor, an impedance sensor, a hydrostatic sensor, or a hydroacoustic sensor.

5. The device of claim 4, wherein the one or more sensors are one or more impedance sensors and wherein the precast concrete segments forming the one or more chutes include smart concrete, the smart concrete in the one or more chutes serving as transducers to create an electric field in the one or more chutes, the one or more impedance sensors being responsive to changes to the electric field in the one or more chutes.

6. The device of claim 1, further including a communications module adapted to receive a sensor signal from the one or more sensors and transmit a communications signal corresponding to the sensor signal.

7. The device of claim 6, further including a processor:
operatively coupled to the one or more sensor and configured to determine (i) a number of animals traveling through individual chutes or a combination of the chutes, or (ii) a volume of animals traveling through the aquatic animal passage system; and
configured to provide a representation of the number or volume determined to the communication module.

8. The device of claim 1, wherein the one or more sensors are further adapted to sense a direction of movement of an animal passing through aquatic animal passage system.

9. The device of claim 1, wherein the precast concrete segments are further adapted to interconnected with an adjacent waterway barrier.

10. The device of claim 1, wherein the aquatic animal passage system defines: a fish ladder or an eel passage system.

* * * * *